United States Patent
Jackwood

(10) Patent No.: US 9,732,144 B2
(45) Date of Patent: Aug. 15, 2017

(54) INFECTIOUS BURSAL DISEASE (IBDV) VACCINE COMPOSITIONS

(71) Applicant: Ohio State Innovation Foundation, Columbus, OH (US)

(72) Inventor: Daral John Jackwood, Wooster, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 4 days.

(21) Appl. No.: 13/982,714

(22) PCT Filed: Jul. 5, 2013

(86) PCT No.: PCT/US2013/049453
§ 371 (c)(1),
(2) Date: Jul. 30, 2013

(87) PCT Pub. No.: WO2014/008475
PCT Pub. Date: Jan. 9, 2014

(65) Prior Publication Data
US 2015/0104475 A1  Apr. 16, 2015

Related U.S. Application Data

(60) Provisional application No. 61/668,314, filed on Jul. 5, 2012.

(51) Int. Cl.
*A61K 39/295* (2006.01)
*A61K 39/12* (2006.01)
(Continued)

(52) U.S. Cl.
CPC ............ *C07K 16/10* (2013.01); *A61K 38/162* (2013.01); *A61K 39/12* (2013.01); *C12N 7/00* (2013.01);
(Continued)

(58) Field of Classification Search
None
See application file for complete search history.

(56) References Cited

U.S. PATENT DOCUMENTS 5,605,827 A * 2/1997 Jackwood ............ C07K 14/005
435/235.1
6,764,684 B2 * 7/2004 Saitoh et al. ............... 424/199.1
(Continued)

FOREIGN PATENT DOCUMENTS

WO   2005071068 A1   8/2005
WO   WO 2007/009673   1/2007
(Continued)

OTHER PUBLICATIONS

Lee et al., "Crystal Structure of infectious bursal disease virus VP2 subviral particle at 2.6 A resolution: Implications in virion assembly and immunogenicity," Journal of Structural Biology, 155: 74-86 (2006).*

(Continued)

*Primary Examiner* — Janet L Andres
*Assistant Examiner* — M. Franco Salvoza
(74) *Attorney, Agent, or Firm* — Meunier Carlin & Curfman LLC

(57) ABSTRACT

Provided herein are methods and compositions relating to Infectious Bursal Disease Virus (IBDV), and vaccines for treatment and prevention thereof.

27 Claims, 4 Drawing Sheets

(51) Int. Cl.
| | |
|---|---|
| C07K 16/10 | (2006.01) |
| A61K 38/16 | (2006.01) |
| C12N 7/00 | (2006.01) |
| G01N 33/569 | (2006.01) |
| A61K 39/00 | (2006.01) |

(52) U.S. Cl.
CPC ........... *G01N 33/56983* (2013.01); *A61K 2039/5258* (2013.01); *A61K 2039/545* (2013.01); *A61K 2039/552* (2013.01); *C07K 2317/76* (2013.01); *C12N 2720/10022* (2013.01); *C12N 2720/10023* (2013.01); *C12N 2720/10034* (2013.01); *C12N 2799/026* (2013.01); *G01N 2333/08* (2013.01)

(56) References Cited

U.S. PATENT DOCUMENTS

| | | | |
|---|---|---|---|
| 2003/0152592 A1* | 8/2003 | Boot | C07K 14/005 424/233.1 |
| 2004/0234949 A1* | 11/2004 | Ruiz Caston | A61K 39/12 435/5 |
| 2007/0041999 A1 | 2/2007 | Rasochova | 549/532 |
| 2007/0128692 A1* | 6/2007 | Aguirre | C07K 14/005 435/69.1 |
| 2007/0207526 A1* | 9/2007 | Coit | A61K 39/12 435/91.1 |
| 2011/0190164 A1 | 8/2011 | Zurcher | 424/185.1 |

FOREIGN PATENT DOCUMENTS

| | | |
|---|---|---|
| WO | WO 2009/103752 | 8/2009 |
| WO | WO 2014/008475 | 1/2014 |

OTHER PUBLICATIONS

Tacken et al. ("Infectious Bursal Disease Virus Capsid Protein VP3 Interacts both with VP1, the RNA-Dependent RNA Polymerase, and with Viral Double-Stranded RNA," vol. 76, No. 22: 11301-11311 (2002).*
Yuan et al., "Canine Parvovirus Capsid Assembly and Differences in Mammalian and Insect Cells," Virology vol. 279, Issue 2: 546-557 (2001).*
Deng et al., "Antigenic structure analysis of VP3 of infectious bursal disease virus," Virus Research 129: 35-42 (2007).*
Birghan C, et al. (2000) A non-canonical Lon proteinase lacking the ATPase domain employs the Ser-Lys catalytic dyad to exercise broad control over the life cycle of a double-stranded RNA virus. EMBO J, 19:114-23.
Caston JR, et al. (2001) C terminus of infectious bursal disease virus major capsid protein VP2 is involved in definition of the T number for capsid assembly. J Virol, 75(22):10815-28.
Coulibaly F, et al. (2005) The Birnavirus crystal structure reveals structural relationships among icosahedral viruses. Cell, 120:761-72.
Coulibaly F, et al. (2010) Crystal structure of an aquabirnavirus particle: Insights into antigenic diversity and virulence determinism. J Virol, 84:1792-9.
Dobos P, et al. (1979) Biophysical and Biochemical Characterization of Five Animal Viruses with Bisegmented Double-Stranded RNA Genomes. J Virol, 32:593-605.
Dybing JK, et al. (1998) Antigenic and immunogenic properties of baculovirus-expressed infectious bursal disease viral proteins. Avian Dis, 42:80-91.
Eterradossi N, et al. (1997) Modified activity of a VP2-located neutralizing epitope on various vaccine, pathogenic and hypervirulent strains of infectious bursal disease virus. Arch Virol, 142:255-70.

Eterradossi N, et al. (1998) Critical amino acid changes in VP2 variable domain are associated with typical and atypical antigenicity in very virulent infectious bursal disease viruses. Arch Virol, 143:1627-36.
Galloux M, et al. (2007) Infectious Bursal Disease Virus, a Non-enveloped Virus, Possesses a Capsid-associated Peptide that Deforms and Perforates Biological Membranes. J Biol Chem, 282:20774-84.
Heine HG, et al. (1991) Sequence analysis and expression of the host-protective immunogen VP2 of a variant strain of infectious bursal disease virus which can circumvent vaccination with standard type I strains. J Gen Virol, 72:1835-43.
Jackwood DJ, et al. (2001) Amino Acid Comparison of Infectious Bursal Disease Viruses Placed in the Same or Different Molecular Groups by RT/PCR-RFLP. Avian Dis, 45:330-9.
Jackwood DJ, et al. (2005) Infectious Cursal Disease Virus Isolate MO195 VP2 protein (VP2) Gene. GenBank Accession Version: AY780324.1.
Jackwood DJ, et al. (2005) Molecular epidemiology of infectious bursal disease viruses: Distribution and genetic analysis of newly emerging viruses in the United States. Avian Dis, 49:220-6.
Jackwood DJ, et al. (2005) Molecular studies on suspect very virulent infectious bursal disease virus genomic RNA samples. Avian Dis, 49:246-51.
Jackwood DJ, et al. (2009) Infectious Bursal Disease Virus Isolate USA08MD34p VP2 (VP2) Gene. GenBank Accession Version: GQ856676.1.
Jackwood DJ, et al. (2010) Detection and characterization of infectious bursal disease viruses in broilers at processing. Preventive Vet Med, 97:45-50.
Jackwood DJ, et al. (2011) Amino acids contributing to antigenic drift in the infectious bursal disease Birnavirus (IBDV). Virol, 409:33-7.
Kibenge FSB, et al. (1988) Biochemistry and Immunology of Infectious Bursal Disease Virus. J Gen Virol, 69:1757-75.
Kibenge FSB, et al. (1990) Nucleotide sequence analysis of genome segment A of infectious bursal disease virus. J Gen Virol, 71:569-77.
Letzel T, et al. (2007) Molecular and structural bases for the antigenicity of VP2 of infectious bursal disease virus. J Virol, 81:12827-35.
Lombardo E, et al. (1999) VP1, the putative RNA-dependent RNA polymerase of infectious bursal disease virus, forms complexes with the capsid protein VP3, leading to efficient encapsidation into virus-like particles. J Virol, 73:6973-83.
Maraver A, et al. (2003) Identification and Molecular Characterization of the RNA Polymerase-Binding Motif of Infectious Bursal Disease Virus Inner Capsid Protein VP3. J Virol, 77(4):2459-68.
Martinez-Torrecuadrada JL, et al. (2000) Antigenic Properties and Diagnostic Potential of Baculovirus-Expressed Infectious Bursal Disease Virus Proteins VPX and VP3. Clin and Diag Lab Immunol, 7:645-51.
Martinez-Torrecuadrada JL, et al. (2000) Different Architectures in the Assembly of Infectious Bursal Disease Virus Capsid Proteins Expressed in Insect Cells. Virol, 278:322-31.
Martinez-Torrecuadrada JL, et al. (2003) Structure-dependent efficacy of infectious bursal disease virus (IBDV) recombinant vaccines. Vaccine, 21:1952-60.
Ona A, et al. (2004) The C-terminal domain of the pVP2 precursor is essential for the interaction between VP2 and VP3, the capsid polypeptides of infectious bursal disease virus. Virol, 322:135-42.
Pitcovski J, et al. (1996) Insect cell-derived VP2 of infectious bursal disease virus confers protection against the disease in chickens. Avian Dis, 40:753-61.
Schnitzler D, et al. (1993) The genetic basis for the antigenicity of the VP2 protein of the infectious bursal disease virus. J Gen Virol, 74:1563-71.
Vakharia VN, et al. (1993) Infectious bursal disease virus structural proteins expressed in a baculovirus recombinant confer protection in chickens. J Gen Virol, 74:1201-6.
Vakharia VN, et al. (1994) Active and passive protection against variant and classic infectious bursal disease virus strains induced by baculovirus-expressed structural proteins. Vaccine, 12:452-6.

(56) References Cited

OTHER PUBLICATIONS

Vakharia VN, et al. (1994) Molecular basis of antigenic variation in infectious bursal disease virus. Virus Res, 31:265-73.
van den Berg TP, et al. (2000) Infectious bursal disease (Gumboro Disease). World Trade and Public Health Implications, OIE Scientific and Technical Rev, 19:509-43.
von Einem UI, et al. (2004) VP1 of infectious bursal disease virus is an RNA-dependent RNA polymerase. J Gen Virol, 85:2221-9.
International Search Report and Written Opinion issued Feb. 18, 2014 by the International Searching Authority for PCT/US13/49453, which was filed Jul. 5, 2013 and published as WO 2014/008475 on Jan. 9, 2014 [Applicant—The Ohio State University; Inventor—Dharal J. Jackwood] [15 pages].
Yu-Chen and William E. Bentley, "Effect of MOI ratio on the composition and yield of chimeric infectious bursal disease virus-like particles by baculovirus co-infection: Deterministic predictions and experimental results", Biotechnology and Bioengineering 20011005 John Wiley and Sons Inc., vol. 75, No. 1, 2001, pp. 104-119.
Hu, Y et al., "Chimeric infectious bursal disease virus-like particles expressed in insect cells and purified by immobilized metal affinity chromatography", Biotechnology and Bioengineering, Wiley & Sons, vol. 63, No. 6, 1999, pp. 721-729.
Jackwood, Daral, Multivalent Virus-Like-Particle Vaccine Protects Against Classic and Variant Infectious Bursal Disease Viruses:, Avian Disease, vol. 57, No. 1, 2013, pp. 41-50.
Supplementary European Search Report, issued in European Application No. EP 13812988, dates Feb. 5, 2016.

\* cited by examiner

Figure 3A. pVP2 clones excised from pVL1393 using *Eco*RI.

Figure 3B. VP3 clones excised from pVL1393 using *Eco*RI.

SEQUENCE LISTING

<160> NUMBER OF SEQ ID NOS: 24

<210> SEQ ID NO 1
<211> LENGTH: 31
<212> TYPE: DNA
<213> ORGANISM: Artificial Sequence
<220> FEATURE:
<223> OTHER INFORMATION: synthetic construct; VP3F primer

<400> SEQUENCE: 1
gtacctgatc accatggctg catcagagtt c                           31

<210> SEQ ID NO 2
<211> LENGTH: 30
<212> TYPE: DNA
<213> ORGANISM: Artificial Sequence
<220> FEATURE:
<223> OTHER INFORMATION: synthetic construct; VP3R primer

<400> SEQUENCE: 2
caggatgatc actcaaggtc ctcatcagag                             30

<210> SEQ ID NO 3
<211> LENGTH: 32
<212> TYPE: DNA
<213> ORGANISM: Artificial Sequence
<220> FEATURE:
<223> OTHER INFORMATION: synthetic construct; VP2F primer

<400> SEQUENCE: 3
ttcgatgatc acgatgacaa acctgtcaga tc                          32

<210> SEQ ID NO 4
<211> LENGTH: 31
<212> TYPE: DNA
<213> ORGANISM: Artificial Sequence
<220> FEATURE:
<223> OTHER INFORMATION: synthetic construct; VP2R primer

<400> SEQUENCE: 4
actactgatc acccttgtc ggcggcgaga g                            31

<210> SEQ ID NO 5
<211> LENGTH: 18
<212> TYPE: DNA
<213> ORGANISM: Artificial Sequence
<220> FEATURE:
<223> OTHER INFORMATION: synthetic construct; VP2 primer

<400> SEQUENCE: 5
gcccagagtc tacaccat                                          18

<210> SEQ ID NO 6
<211> LENGTH: 18
<212> TYPE: DNA
<213> ORGANISM: Artificial Sequence
<220> FEATURE:
<223> OTHER INFORMATION: synthetic construct; VP2 primer

<400> SEQUENCE: 6
cccggattat gtctttga                                          18

<210> SEQ ID NO 7
<211> LENGTH: 801
<212> TYPE: DNA
<213> ORGANISM: Infectious bursal disease virus

<400> SEQUENCE: 7

```
gtacctgatc accatggctg catcagagtt caaagagacc cctgaactcg agagcgccgt    60
cagagccatg gaggcagcag ccaatgtgga cccactgttc caatctgcac tcagtgtgtt   120
catgtggctg gaagagaatg ggattgtgac tgacatggcc aacttcgcac tcagcgaccc   180
gaacgcccat cggatgcgaa atttcttgc aaacgcacca caagcaggca gcaagtcgca   240
aagggccaag tacgggacag caggctacgg agtggaggcc cggggcccca caccagagga   300
agcacagagg gaaaaagaca cacggatctc aaagaagatg agaccatgg gcatctactt   360
tgcgacaccg gaatgggtag cactcaatgg caccgaggg ccaagcccag ccagctaaa    420
gtactggcag aacacacgag aaataccgga cccaaatgag gactatctag actacgtgca   480
tgcagagaag agccggttgg catcagaaga acaaatccta agggcagcta cgtcgatcta   540
cggggctcca ggacaggcag agccacccca agctttcata gatgaagttg ccaaagtcta   600
tgaaatcaac catggacgtg gccccaacca agaacagatg aaagatctgc tcttgactgc   660
gatggagatg aagcatcgca atcccaggcg ggctccacca agcccaagc caaaacccaa    720
tgctccaaca cagagacccc ctggtcggct gggccgctgg atcaggactg tctctgatga   780
ggaccttgag tgatcatcct g                                              801
```

<210> SEQ ID NO 8
<211> LENGTH: 259
<212> TYPE: PRT
<213> ORGANISM: Infectious bursal disease virus

<400> SEQUENCE: 8

```
Met Ala Ala Ser Glu Phe Lys Glu Thr Pro Glu Leu Glu Ser Ala Val
1               5                   10                  15

Arg Ala Met Glu Ala Ala Asn Val Asp Pro Leu Phe Gln Ser Ala
                20                  25                  30

Leu Ser Val Phe Met Trp Leu Glu Glu Asn Gly Ile Val Thr Asp Met
            35                  40                  45

Ala Asn Phe Ala Leu Ser Asp Pro Asn Ala His Arg Met Arg Asn Phe
        50                  55                  60

Leu Ala Asn Ala Pro Gln Ala Gly Ser Lys Ser Gln Arg Ala Lys Tyr
65                  70                  75                  80

Gly Thr Ala Gly Tyr Gly Val Glu Ala Arg Gly Pro Thr Pro Glu Glu
                85                  90                  95

Ala Gln Arg Glu Lys Asp Thr Arg Ile Ser Lys Lys Met Glu Thr Met
                100                 105                 110

Gly Ile Tyr Phe Ala Thr Pro Glu Trp Val Ala Leu Asn Gly His Arg
            115                 120                 125

Gly Pro Ser Pro Gly Gln Leu Lys Tyr Trp Gln Asn Thr Arg Glu Ile
        130                 135                 140

Pro Asp Pro Asn Glu Asp Tyr Leu Asp Tyr Val His Ala Glu Lys Ser
145                 150                 155                 160

Arg Leu Ala Ser Glu Glu Gln Ile Leu Arg Ala Ala Thr Ser Ile Tyr
                165                 170                 175

Gly Ala Pro Gly Gln Ala Glu Pro Pro Gln Ala Phe Ile Asp Glu Val
                180                 185                 190

Ala Lys Val Tyr Glu Ile Asn His Gly Arg Gly Pro Asn Gln Glu Gln
            195                 200                 205

Met Lys Asp Leu Leu Leu Thr Ala Met Glu Met Lys His Arg Asn Pro
```

```
              210                 215                 220
Arg Arg Ala Pro Pro Lys Pro Lys Pro Lys Pro Asn Ala Pro Thr Gln
225                 230                 235                 240

Arg Pro Pro Gly Arg Leu Gly Arg Trp Ile Arg Thr Val Ser Asp Glu
                245                 250                 255

Asp Leu Glu

<210> SEQ ID NO 9
<211> LENGTH: 1573
<212> TYPE: DNA
<213> ORGANISM: Infectious bursal disease virus

<400> SEQUENCE: 9
aacgatgatc acgatgacaa acctgtcaga tcaaacccaa cagattgttc cgttcatacg      60
gagccttctg atgccaacaa ccggaccggc gtccattccg acgacaccc tggagaagca     120 cactctcagg tcagagacct cgacctacaa tttgactgtg ggggacacag ggtcagggct     180
aattgtcttt ttccctggct tccctggctc aattgtgggt gctcactaca cactgcagag     240
caatgggaac tacaagttca atcagatgct cctgacggca cagaacctac cggccagcta     300
caactactgc aggctagtga gtcggagtct cacagtaagg tcaagcacac tccctggtgg     360
cgtttatgca ctaaacggca ccataaacgc cgtgaccttc caaggaagcc tgagtgaact     420
gacagatgtt agctacaatg ggttgatgtc tgcaacagcc aacatcaacg acaaaatcgg     480
gaacgtccta gtaggggaag gggtcaccgt cctcagctta cccacatcat atgatcttgg     540
gtatgtgagg cttggtgacc ccataccgc tatagggctt gacccaaaaa tggtagcaac     600
atgtgacagc agtgacaggc ccagagtcta caccataact gcagccgata attaccaatt     660
ctcatcacag taccaaacag gtggggtaac aatcacactg ttctcggcca acattgatgc     720
tatcacaagt ctcagcgttg ggggggagct cgtgttcaaa acaagtgtcc aaaaccttgt     780
actgggcgcc accatctacc ttataggctt tgatgggact gcggtaatca ccagagccgt     840
ggccgcaaac aatgggctga cggccggtat cgacaatctt atgccattca atcttgtgat     900
tccgaccaac gagataaccc aaccaatcac atccatcaaa ctggagatag tgacctccaa     960
aagtgatggt caggcagggg aacagatgtc atggtcggca agtgggagcc tagcagtgac    1020
gatccatggt ggcaaccatc caggagccct ccgtcccgtc acactagtgg cctacgaaag    1080
agtggcaaca ggatctgtcg ttacggtcgc tggggtgagc aacttcgagc tgatccccaa    1140
tcctgaacta gcaaagaacc tggttacaga atacggccga tttgaccag gagccatgaa    1200 ctacacaaaa ttaatactga gtgagaggga ccgccttggc atcaagactg tctggccaac    1260
aagggagtac actgactttc gtgagtactt catggaggtg gccgacctca actctccct    1320 gaagattgca ggagcatttg gcttcaaaga cataatccgg gccataagga ggatagctgt    1380
gccggtggtc tctacactgt tcccacctgc tgctcctctg gcccatgcaa ttggggaagg    1440
tgtagactac ctgctgggcg atgaggcaca ggctgcttca ggaactgctc gagccgcgtc    1500
aggaaaagca agggctgcct caggccgcat aaggcagctg actctcgccg ccgacaaggg    1560
gtgatcagta tgt                                                        1573

<210> SEQ ID NO 10
<211> LENGTH: 516
<212> TYPE: PRT
<213> ORGANISM: Infectious bursal disease virus

<400> SEQUENCE: 10
```

-continued

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asn Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
                100                 105                 110

Leu Pro Gly Gly Val Tyr Ala Leu Asn Gly Thr Ile Asn Ala Val Thr
            115                 120                 125

Phe Gln Gly Ser Leu Ser Glu Leu Thr Asp Val Ser Tyr Asn Gly Leu
130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
                180                 185                 190

Met Val Ala Thr Cys Asp Ser Ser Asp Arg Pro Arg Val Tyr Thr Ile
                195                 200                 205

Thr Ala Ala Asp Asn Tyr Gln Phe Ser Ser Gln Tyr Gln Thr Gly Gly
            210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Asn Leu Val
                245                 250                 255

Leu Gly Ala Thr Ile Tyr Leu Ile Gly Phe Asp Gly Thr Ala Val Ile
                260                 265                 270

Thr Arg Ala Val Ala Ala Asn Asn Gly Leu Thr Ala Gly Ile Asp Asn
            275                 280                 285

Leu Met Pro Phe Asn Leu Val Ile Pro Thr Asn Glu Ile Thr Gln Pro
            290                 295                 300

Ile Thr Ser Ile Lys Leu Glu Ile Val Thr Ser Lys Ser Asp Gly Gln
305                 310                 315                 320

Ala Gly Glu Gln Met Ser Trp Ser Ala Ser Gly Ser Leu Ala Val Thr
                325                 330                 335

Ile His Gly Gly Asn His Pro Gly Ala Leu Arg Pro Val Thr Leu Val
            340                 345                 350

Ala Tyr Glu Arg Val Ala Thr Gly Ser Val Val Thr Val Ala Gly Val
            355                 360                 365

Ser Asn Phe Glu Leu Ile Pro Asn Pro Glu Leu Ala Lys Asn Leu Val
            370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415
```

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
    450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
        500                 505                 510

Ala Asp Lys Gly
        515

<210> SEQ ID NO 11
<211> LENGTH: 1573
<212> TYPE: DNA
<213> ORGANISM: Infectious bursal disease virus

<400> SEQUENCE: 11
aacgatgatc acgatgacaa acctgtcaga tcaaacccaa cagattgttc cgttcatacg      60
gagccttctg atgccaacaa ccggaccggc gtccattccg gacgacaccc tggagaagca     120
cactctcagg tcagagacct cgacttacaa tttgactgtg ggggacacag ggtcagggct     180
aattgtcttt ttccctggat tccctggctc aattgtgggt gctcactaca cactgcagag     240
caatgggaac tacaagttcg atcagatgct cctgactgcc cagaacctac cggccagcta     300
caactactgc aggctagtga gtcggagtct cacagtaagg tcaagcacac tccctggtgg     360
cgtttatgca ctaaacggca ccataaacgc cgtgaccttc aaggaagcct gagtgagct      420 gacagatgtt agctacaatg ggttgatgtc tgcaacagcc aacatcaacg acaaaattgg     480
gaacgtccta gtaggggaag gagtcaccgt cctcagccta cccacatcat atgatcttgg     540
gtatgtgagg cttggtgacc ccatacccgc tatagggctt gacccaaaaa tggtagcaac     600
atgtgacagc agtgacaggc ccagagtcta caccataact gcagctgatg attaccaatt     660
ctcatcacag taccaaccag gtggggtaac aatcacactg ttctcagcca acattgatgc     720
catcacaagc ctcagcgtcg ggggagagct cgtgttcaaa accagcgtcc aaagccttgt     780
actgggcgcc accatctacc tcataggatt tgatgggact gcggtaatca ccagagctgt     840
ggccgcaaac aatgggctga cggccggcat cgacaatctt atgccattca atcttgtgat     900
tccaaccaac gagataaccc agccaatcac atccatcaaa ttggagatag ttacctccaa     960
aagtagtggt caggaagggg atcagatgtc atggtcggca agtgggagcc tagcagtgac    1020
gatccatggt ggcaactatc cagggcccct ccgtcccgtc acactagtag cttacgaaag    1080
agtggcaaca ggatctgtcg ttacggtcgc tggggtgagc aacttcgagc tgatcccaaa    1140
tcctgaacta gcaaagaacc tggttacaga atacggccga tttgacccag agccatgaa    1200 ctacacaaaa ttgatactga gtgagaggga ccgtcttggc atcaagaccg tctggccaac    1260
aagggagtac actgactttc gtgagtactt catggaggtg gccgacctca actctcccct    1320
gaagattgca ggagcatttg gcttcaaaga tattatccgg gccataagga ggatagctgt    1380
gccggtggtc tctacattgt tcccacctgc tgctccccta gcccatgcaa ttggggaagg    1440
tgtagactac ctgctgggcg atgaggcaca ggctgcttca ggaactgctc gagccgcgtc    1500

```
aggaaaagca agggctgcct caggccgcat aaggcagcta actctcgccg ccgacaaggg    1560
gtgatcagta tgt                                                      1573
```

<210> SEQ ID NO 12
<211> LENGTH: 516
<212> TYPE: PRT
<213> ORGANISM: Infectious bursal disease virus

<400> SEQUENCE: 12

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Ile Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Ser Gly Gln
305                 310                 315                 320

Glu Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
```

```
                355              360              365
Ser Asn Phe Glu Leu Ile Pro Asn Pro Glu Leu Ala Lys Asn Leu Val
    370              375              380

Thr Glu Tyr Gly Arg Phe Asp Pro Gly Ala Met Asn Tyr Thr Lys Leu
385              390              395             400

Ile Leu Ser Glu Arg Asp Arg Leu Gly Ile Lys Thr Val Trp Pro Thr
                405              410              415

Arg Glu Tyr Thr Asp Phe Arg Glu Tyr Phe Met Glu Val Ala Asp Leu
            420              425              430

Asn Ser Pro Leu Lys Ile Ala Gly Ala Phe Gly Phe Lys Asp Ile Ile
                435              440              445

Arg Ala Ile Arg Arg Ile Ala Val Pro Val Val Ser Thr Leu Phe Pro
    450              455              460

Pro Ala Ala Pro Leu Ala His Ala Ile Gly Glu Gly Val Asp Tyr Leu
465              470              475             480

Leu Gly Asp Glu Ala Gln Ala Ala Ser Gly Thr Ala Arg Ala Ala Ser
                485              490              495

Gly Lys Ala Arg Ala Ala Ser Gly Arg Ile Arg Gln Leu Thr Leu Ala
                500              505              510

Ala Asp Lys Gly
        515

<210> SEQ ID NO 13
<211> LENGTH: 801
<212> TYPE: DNA
<213> ORGANISM: Infectious bursal disease virus

<400> SEQUENCE: 13
gtacctgatc accatggctg catcagagtt caaagagacc cccgaactcg agagtgccgt    60
cagagcaatg gaagcagcag ccaacgtgga cccactattc aatctgcac tcagtgtgtt   120 catgtggctg aagagaatg ggattgtgac tgacatggcc aacttcgcac tcagcgaccc   180
gaacgcccat cggatgcgaa atttttcttgc aaacgcacca caagcaggca gcaagtcgca   240
aagggccaag tacgggacag caggctacgg agtggaggct cggggccccg cgccagagga   300
agcacagagg gaaaaagaca cacggatctc aaagaagatg gagaccatgg gcatctactt   360
tgcaacacca gaatgggtag cactcaatgg caccgaggg ccaagccccg gccagctaaa   420
gtactggcag agcacacgag aaataccgga cccaaacgag gactatctag actacgtgca   480
tgcagagaag agccggttgg catcagaaga acaaatccta agggcagcta cgtcgatcta   540
cggggctcca ggacaggcag agccacccca gctttcata gacgaagttg ccaaagtcta   600
tgaaatcaac catggacgtg gcccaaacca agaacagatg aaagatctgc tcttgactgc   660
gatggagatg aagcatcgca atcccaggcg ggctctacca agcccaagc caaaacccaa   720 tgctccaaca cagagacccc ctggtcggct gggccgctgg atcaggaccg tctctgatga   780
ggaccttgag tgatcatcct g                                             801

<210> SEQ ID NO 14
<211> LENGTH: 259
<212> TYPE: PRT
<213> ORGANISM: Infectious bursal disease virus

<400> SEQUENCE: 14

Met Ala Ala Ser Glu Phe Lys Glu Thr Pro Glu Leu Glu Ser Ala Val
1               5                   10                  15
```

```
Arg Ala Met Glu Ala Ala Ala Asn Val Asp Pro Leu Phe Gln Ser Ala
            20                  25                  30
Leu Ser Val Phe Met Trp Leu Glu Glu Asn Gly Ile Val Thr Asp Met
        35                  40                  45
Ala Asn Phe Ala Leu Ser Asp Pro Asn Ala His Arg Met Arg Asn Phe
    50                  55                  60
Leu Ala Asn Ala Pro Gln Ala Gly Ser Lys Ser Gln Arg Ala Lys Tyr
65                  70                  75                  80
Gly Thr Ala Gly Tyr Gly Val Glu Ala Ar

```
tgctccaaca cagagacccc ctggtcggct gggccgctgg atcaggaccg cctctgatga      780
ggaccttgag tgatcatcct g                                                801
```

<210> SEQ ID NO 16
<211> LENGTH: 259
<212> TYPE: PRT
<213> ORGANISM: Infectious bursal disease virus

<400> SEQUENCE: 16

```
Met Ala Ala Ser Glu Phe Lys Glu Thr Pro Glu Leu Glu Ser Ala Val
1               5                   10                  15

Arg Ala Met Glu Ala Ala Asn Val Asp Pro Leu Phe Gln Ser Ala
            20                  25                  30

Leu Ser Val Phe Met Trp Leu Glu Glu Asn Gly Ile Val Thr Asp Met
        35                  40                  45

Ala Asn Phe Ala Leu Ser Asp Pro Asn Ala His Arg Met Arg Asn Phe
    50                  55                  60

Leu Ala Asn Ala Pro Gln Ala Gly Ser Lys Ser Gln Arg Ala Lys Tyr
65                  70                  75                  80

Gly Thr Ala Gly Tyr Gly Val Glu Ala Arg Gly Pro Thr Pro Glu Glu
                85                  90                  95

Ala Gln Arg Glu Lys Asp Thr Arg Ile Ser Lys Lys Met Glu Thr Met
            100                 105                 110

Gly Ile Tyr Phe Ala Thr Pro Glu Trp Val Ala Leu Asn Gly His Arg
        115                 120                 125

Gly Pro Ser Pro Gly Gln Leu Lys Tyr Trp Gln Asn Thr Arg Glu Ile
    130                 135                 140

Pro Asp Pro Asn Glu Asp Tyr Leu Asp Tyr Val His Ala Glu Lys Ser
145                 150                 155                 160

Arg Leu Ala Ser Glu Glu Gln Ile Leu Arg Ala Ala Thr Ser Ile Tyr
                165                 170                 175

Gly Ala Pro Gly Gln Ala Glu Pro Pro Gln Ala Phe Ile Asp Glu Val
            180                 185                 190

Ala Lys Val Tyr Glu Ile Asn His Gly Arg Gly Pro Asn Gln Glu Gln
        195                 200                 205

Met Lys Asp Leu Leu Leu Thr Ala Met Glu Met Lys His Arg Asn Pro
    210                 215                 220

Arg Arg Ala Leu Pro Lys Pro Lys Pro Lys Pro Asn Ala Pro Thr Gln
225                 230                 235                 240

Arg Pro Pro Gly Arg Leu Gly Arg Trp Ile Arg Thr Ala Ser Asp Glu
                245                 250                 255

Asp Leu Glu
```

<210> SEQ ID NO 17
<211> LENGTH: 1573
<212> TYPE: DNA
<213> ORGANISM: Infectious bursal disease virus

<400> SEQUENCE: 17

```
aacgatgatc acgatgacaa acctgtcaga tcaaacccaa cagattgttc cgttcatacg      60
gagccttctg atgccaacaa ccggaccggc gtccattccg gacgacaccc tggagaagca     120
cactctcagg tcagagacct cgacctacaa tttgactgtg ggggacacag ggtcagggct     180
aattgtcttt ttccctggat tccctggctc aattgtgggt gctcactaca cactgcagag     240
caatgggaac tacaagttcg atcagatgct cctgactgcc cagaacctac cggccagtta     300
```

```
caactactgc aggctagtga gtcggagtct cacagtgagg tcaagcacac ttcctggtgg    360
cgtttatgca ctaaacggca ccataaacgc cgtgaccttc aaggaagcc  tgagtgaact    420
gacagatgtt agctacaatg ggttgatgtc tgcaacagcc aacatcaacg acaaaattgg    480
gaacgtccta gtaggggaag gggtcaccgt cctcagctta cccacatcat atgatcttgg    540
gtatgtgagg cttggtgacc ccattccgc  aatagggctt gacccaaaaa tggtagccac    600
atgtgacagc agtgacaggc ccagagtcta caccataact gcagccgatg attaccaatt    660
ctcatcacag taccaaccag gtggggtaac aatcacactg ttctcagcca acattgatgc    720
catcacaagc ctcagcgttg ggggagagct cgtgtttcaa acaagcgtcc acggccttgt    780
actgggcgcc accatctacc tcataggctt tgatgggaca gcggtaatca ccagggctgt    840
ggccgcaaac aatgagctga cgaccggcac cgacaacctt ttgccattca atcttgtgat    900
tccaacaaac gagataaccc agccaatcac atccatcaaa ctggagatag tgacctccaa    960
aagtggtggt caggcagggg atcagatgtc atggtccgca agagggagcc tagcagtgac   1020
gatccatggt ggcaactatc cagggccct  ccgtcccgtc acgctagtgg cctacgaaag   1080
agtggcaaca ggatccgtcg ttacggtcgc tggggtgagc aacttcgagc tgatcccaaa   1140
tcctgaacta gcaaagaacc tggttacaga atacggccga tttgacccag agccatgaa   1200
ctacacaaaa ttgatactga gtgagaggga ccgtcttggc atcaagaccg tctggccaac   1260
aagggagtac actgactttc gtgaatactt catggaggtg gccgacctca actctcccct   1320
gaagattgca ggagcattcg gcttcaaaga cataatccgg gccataagga ggatagctgt   1380
gccggtggtc tccacattgt tcccacctgc cgctcccta  gcccatgcaa ttggggaagg   1440
tgtagactac ctgctgggcg atgaggcaca ggctgcttca ggaactgctc gagccgcgtc   1500
aggaaaagca agagctgcct cgggccgcat aaggcagctg actctcgccg ccgacaaggg   1560
gtgatcagta gta                                                     1573
```

<210> SEQ ID NO 18
<211> LENGTH: 516
<212> TYPE: PRT
<213> ORGANISM: Infectious bursal disease virus

<400> SEQUENCE: 18

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140
```

```
Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
            165                 170                 175

Tyr Val Arg Leu Gly Asp Pro Ile Pro Ala Ile Gly Leu Asp Pro Lys
        180                 185                 190

Met Val Ala Thr Cys Asp Ser Ser Asp Arg Pro Arg Val Tyr Thr Ile
    195                 200                 205

Thr Ala Ala Asp Asp Tyr Gln Phe Ser Ser Gln Tyr Gln Pro Gly Gly
210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Gln Thr Ser Val His Gly Leu Val
            245                 250                 255

Leu Gly Ala Thr Ile Tyr Leu Ile Gly Phe Asp Gly Thr Ala Val Ile
        260                 265                 270

Thr Arg Ala Val Ala Ala Asn Asn Glu Leu Thr Thr Gly Thr Asp Asn
    275                 280                 285

Leu Leu Pro Phe Asn Leu Val Ile Pro Thr Asn Glu Ile Thr Gln Pro
290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
            325                 330                 335

Ile His Gly Gly Asn Tyr Pro Gly Ala Leu Arg Pro Val Thr Leu Val
        340                 345                 350

Ala Tyr Glu Arg Val Ala Thr Gly Ser Val Val Thr Val Ala Gly Val
    355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
            405                 410                 415

Arg Glu Tyr Thr Asp Phe Arg Glu Tyr Phe Met Glu Val Ala Asp Leu
        420                 425                 430

Asn Ser Pro Leu Lys Ile Ala Gly Ala Phe Gly Phe Lys Asp Ile Ile
    435                 440                 445

Arg Ala Ile Arg Arg Ile Ala Val Pro Val Val Ser Thr Leu Phe Pro
450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
            485                 490                 495

Gly Lys Ala Arg Ala Ala Ser Gly Arg Ile Arg Gln Leu Thr Leu Ala
        500                 505                 510

Ala Asp Lys Gly
        515

<210> SEQ ID NO 19
<211> LENGTH: 1572
<212> TYPE: DNA
<213> ORGANISM: Infectious bursal disease virus
<220> FEATURE:
```

<220> NAME/KEY: misc_feature
<222> LOCATION: (991)..(991)
<223> OTHER INFORMATION: n is a, c, g, or t

<400> SEQUENCE: 19

```
aacgatgatc acgatgacaa acctgtcaga tcaaacccaa cagattgttc cgttcatacg      60
gagccttctg atgccaacaa ccggaccggc gtccattccg gacgacaccc tggagaagca     120
cactctcagg tcagagacct cgacctacaa tttgactgtg ggggacacag ggtcagggct     180
aattgtcttt ttccctggat tccctggctc aattgtgggt gctcactaca cactgcagag     240
caatgggaac tacaagttcg atcagatgct cctgactgcc cagaacctac cggccagcta     300
caactactgc aggctagtga gtcggagtct cacagtaagg tcaagcacac tccctggtgg     360
cgtttatgca ctaaacggca ccataaacgc cgtgaccttc caaggaagcc tgagtgaact     420
gacagatgtt agctacaatg ggttgatgtc tgcaacagcc aacatcaacg acaaaattgg     480
gaacgttcta gtaggggaag gggtaacagt cctcagctta cccacatcat atgatcttgg     540
gtatgtgagg cttggtgacc ccataccctgc tataggactt gacccaaaaa tggtagctac     600
atgtgacagc agtgacaggc ccagagtcta caccataact gcagctgata attaccagtt     660
ctcatcacag taccaaacag gtggggtaac aatcacactg ttctcagcca acattgatgc     720
catcacaagt ctcagcgttg ggggagagct tgtgttcaaa acaagcgtcc aaaaccttgt     780
actgggtgcc accatctacc ttataggctt tgatgggact gcggtaatca ccagagctgt     840
ggccgcaaac aatgggctga cggccggcat cgacaatctt atgccattca accttgtgat     900
tccaaccaat gagataaccc agccaatcac atccatcaaa ctagagatag tgacctccaa     960
aagcaatggg caggcagagg atcagatgtc ntggtcggca agtgggagcc tggcagtgac    1020
gatccatggt ggcaactatc caggagccct ccgtcccgtc acactggtgg cctacgaaag    1080
agtggcaaca ggatctgtcg ttacggtcgc aggggtgagc aacttcgagc tgatcccaaa    1140
tcctgaactg gcaaagaacc tggttacaga atacggccga tttgacccag gagccatgaa    1200
ctacacgaaa ttgatactga gtgagaggga ccgtcttggc atcaagaccg tctggccaac    1260
aagggagtac actgactttc gtgagtactt catggaggtg gccgacctca actctccccct    1320
gaagattgca ggagcatttg gattcaagga cataatccgg gccataagga ggatagctgt    1380
gccggtggtc tctacattgt tcccacctgc cgctcctcta gcccatgcaa ttggggaagg    1440
tgtagactac ctgctgggcg atgaggcaca ggctgcttca ggaactgctc gagccgcgtc    1500
aggaaaagca agggctgcct caggccgcat aaggcagctg actctcgccg ccgacaaggg    1560
gtgatcagta gt                                                       1572
```

<210> SEQ ID NO 20
<211> LENGTH: 516
<212> TYPE: PRT
<213> ORGANISM: Infectious bursal disease virus

<400> SEQUENCE: 20

```
Met Thr Asn Leu Ser Asp Gln Thr Gln Gln Ile Val Pro Phe Ile Arg
  1               5                  10                  15

Ser Leu Leu Met Pro Thr Thr Gly Pro Ala Ser Ile Pro Asp Asp Thr
                 20                  25                  30

Leu Glu Lys His Thr Leu Arg Ser Glu Thr Ser Thr Tyr Asn Leu Thr
             35                  40                  45

Val Gly Asp Thr Gly Ser Gly Leu Ile Val Phe Phe Pro Gly Phe Pro
         50                  55                  60
```

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Asn Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Ile Asp Asn
        275                 280                 285

Leu Met Pro Phe Asn Leu Val Ile Pro Thr Asn Glu Ile Thr Gln Pro
290                 295                 300

Ile Thr Ser Ile Lys Leu Glu Ile Val Thr Ser Lys Ser Asn Gly Gln
305                 310                 315                 320

Ala Glu Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
            485                 490                 495

Gly Lys Ala Arg Ala Ala Ser Gly Arg Ile Arg Gln Leu Thr Leu Ala
        500                 505                 510

Ala Asp Lys Gly
        515

<210> SEQ ID NO 21
<211> LENGTH: 1573
<212> TYPE: DNA
<213> ORGANISM: Infectious bursal disease virus

<400> SEQUENCE: 21

```
aacgatgatc acgatgacaa acctgtcaga tcaaacccaa cagattgttc cgttcatacg      60
gagccttctg atgccaacaa ccggaccggc gtccattccg gacgacaccc tagagaagca     120
cactctcagg tcagagacct cgacctacaa tttgactgtg ggggacacag ggtcagggct     180
aattgtcttt ttccctggtt tccctggctc aattgtgggt gctcactaca cactgcagag     240
caatgggagc tacaagttcg atcagatgct cctgactgcc agaacctac cggccagcta     300
caactactgc aggctagtga gtcggagtct cacagtgagg tcaagcacac tccctggtgg     360
cgtttatgct ctaaatggca ccataaacgc cgtgaccttc caaggaagcc tgagtgaact     420
gacagatgtt agctacaatg ggttgatgtc tgcaacagcc aacatcaacg acaaaatcgg     480
gaacgtccta gtaggggaag gggtaacagt cctcagctta cctacatcat cgatcttgg     540
gtatgtgaga ctcggtgacc ccattccggc tatagggctc gacccaaaaa tggtagcaac     600
atgtgacagc agtgacagac ccagagtcta caccataact gcagccgatg attaccaatt     660
ctcatcacag taccaagcag gtggggtaac aatcacactg ttctcagcta atatcgatgc     720
catcacaagc ctcagcatcg gggggaact cgtgtttcaa acaagcgtcc aaggcctcat     780
actgggtgct accatctacc ttataggctt tgatgggact gcggtaatca ccagagctgt     840
ggcagcagac aatgggctaa cggccggcac tgacaacctt atgccattca acattgtgat     900
tccaaccagc gagataaccc agccaatcac atccatcaaa ctggagatag tgacctccaa     960
aagtggtggt caggcggggg atcagatgtc atggtccgca gtgggagcc tagcagtgac    1020
gatccacggt ggcaactacc caggggcccct ccgtcccgtc acactagtag cctatgaaag    1080
agtggcaaca gggtctgtcg ttacggtcgc tggggtgagc aacttcgagc tgatcccaaa    1140
tcctgaacta gcaaagaacc tggtcacaga atacggccga tttgacccag gggctatgaa    1200
ctacacaaaa ttaatactga gtgagaggga ccgtcttggc atcaagaccg tatggccaac    1260
gagggagtac actgactttc gcgagtactt catggaggtg gccgacctca actctcccct    1320
gaagattgca ggagcatttg gcttcaaaga cataattcgg gctctaagga ggatagctgt    1380
gccggtggtc tctacactgt tcccaccagc cgctcccta gcccatgcaa ttggggaagg    1440
tgtagactac ctgctgggcg atgaggcaca ggctgcttca ggaactgctc gagccgcgtc    1500
aggaaaagca agagctgcct caggtcgcat aaggcagcta actctcgccg ccgacaaggg    1560
gtgatcagta gta                                                        1573
```

<210> SEQ ID NO 22
<211> LENGTH: 516
<212> TYPE: PRT
<213> ORGANISM: Infectious bursal disease virus

<400> SEQUENCE: 22

-continued

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
                35                  40                  45

Val Gly Asp Thr Gly Ser Gly Leu Ile Val Phe Phe Pro Gly Phe Pro
50                  55                  60

Gly Ser Ile Val Gly Ala His Tyr Thr Leu Gln Ser Asn Gly Ser Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
                115                 120                 125

Phe Gln Gly Ser Leu Ser Glu Leu Thr Asp Val Ser Tyr Asn Gly Leu
            130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
                180                 185                 190

Met Val Ala Thr Cys Asp Ser Ser Asp Arg Pro Arg Val Tyr Thr Ile
                195                 200                 205

Thr Ala Ala Asp Asp Tyr Gln Phe Ser Ser Gln Tyr Gln Ala Gly Gly
            210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Ile
                245                 250                 255

Leu Gly Ala Thr Ile Tyr Leu Ile Gly Phe Asp Gly Thr Ala Val Ile
                260                 265                 270

Thr Arg Ala Val Ala Ala Asp Asn Gly Leu Thr Ala Gly Thr Asp Asn
            275                 280                 285

Leu Met Pro Phe Asn Ile Val Ile Pro Thr Ser Glu Ile Thr Gln Pro
            290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
            355                 360                 365

Ser Asn Phe Glu Leu Ile Pro Asn Pro Glu Leu Ala Lys Asn Leu Val
            370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
```

```
             420             425             430
Asn Ser Pro Leu Lys Ile Ala Gly Ala Phe Gly Phe Lys Asp Ile Ile
        435                 440                 445

Arg Ala Leu Arg Arg Ile Ala Val Pro Val Val Ser Thr Leu Phe Pro
    450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510

Ala Asp Lys Gly
        515

<210> SEQ ID NO 23
<211> LENGTH: 1583
<212> TYPE: DNA
<213> ORGANISM: Infectious bursal disease virus

<400> SEQUENCE: 23
gggaattcac tagtgatttt cgatgatcac gatgacaaac ctgtcagatc acacccaaca      60
gattgttccg ttcatacgga gccttctgat gccaacgacc ggaccggcgt ccatcccgga     120
cgacaccctg gagaagcaca cactcaggtc cgaaacctcg acctacaact tgactgtcgg     180
ggacacaggg tcaggactaa ttgtcttttt ccctggattc cctggttcag ttgtaggtgc     240
tcactacaca ctgcagagca gtgggagcta ccagttcgac cagatgctcc tgacagcgca     300
gaacctgcct gcgagctaca actattgcag actagtgagc aggagcctaa ccgtgcggtc     360
aagcacactc cctggtggcg tttatgctct aaatgggacc ataaacgcgg tgaccttcca     420
aggaagcctg agtgagttga ctgactacag ctacaacggg ctgatgtcag ccactgcaaa     480
catcaacgac aagatcggga atgtccttgt tgggaaggg gtgactgtcc taagtctacc     540
aacctcatat gacctcagtt atgtgaggct ggcgacccc atcccagcag caggacttga     600
cccaaagttg atggccacgt gcgacagtag tgatagaccc agagtctaca cagtaacagc     660
cgctgatgag taccaattct cgtcgcaact catcccaagt ggagtgaaga ctacactgtt     720
caccgccaac atcgatgctc ttacaagcct cagtgttggt ggtgagctta tcttcagcca     780
agtaacgatc caaagcattg aagtggacgt caccatttac ttcattgggt cgacgggac      840
agaggtcaca gtcaaagctg ttgcaacaga ctttgggctg acaactggga cgaacaacct     900
tgtgccattc aacctggtgg tcccaacaag tgagatcacc caacccatca cttccatgaa     960
actagaggta gtcacccata aagaggagg cactgctggc gatccgatat catggacagt    1020
gagcgggaca ctagctgtga cagtgcacgg aggcaactat cctggggctc tccgtcccgt    1080
cacccctagtg gcctatgagc gagtggcagc aggatccgtc gtcacagttg cagggggtgag   1140
caacttcgag ctgatcccaa accctgagct tgccaagaac ctagtcacag aatatggccg    1200
atttgacccc ggagcgatga actacaccaa actaatactg agtgagagag atcgtctagg    1260
cataaagact gtctggccaa ccagggagta cactgacttt agagagtact tcatggaagt    1320
tgccgatctc aactcacccct taaagattgc aggtgcgttt ggttttaagg acataatccg    1380
agccatccgg aagattgcgg taccagtggt atccacactc ttcccaccag ctgcaccct     1440
agcccatgca atcggagaag gtgtggatta ccttctgggc gatgaggccc aggcagcctc    1500
agggacggct cgagccgcgt caggaaaagc cagggctgcc tcaggaagaa taaggcagct    1560
```
gactctcgcc gccgacaagg ggt 1583

<210> SEQ ID NO 24
<211> LENGTH: 517
<212> TYPE: PRT
<213> ORGANISM: Infectious bursal disease virus

<400> SEQUENCE: 24

```
Met Thr Asn Leu Ser Asp His Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
50                  55                  60

Gly Ser Val Val Gly Ala His Tyr Thr Leu Gln Ser Ser Gly Ser Tyr
65                  70                  75                  80

Gln Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Tyr Ser Tyr Asn Gly Leu
130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Ser
                165                 170                 175

Tyr Val Arg Leu Gly Asp Pro Ile Pro Ala Ala Gly Leu Asp Pro Lys
            180                 185                 190

Leu Met Ala Thr Cys Asp Ser Ser Asp Arg Pro Arg Val Tyr Thr Val
        195                 200                 205

Thr Ala Ala Asp Glu Tyr Gln Phe Ser Ser Gln Leu Ile Pro Ser Gly
210                 215                 220

Val Lys Thr Thr Leu Phe Thr Ala Asn Ile Asp Ala Leu Thr Ser Leu
225                 230                 235                 240

Ser Val Gly Gly Glu Leu Ile Phe Ser Gln Val Thr Ile Gln Ser Ile
                245                 250                 255

Glu Val Asp Val Thr Ile Tyr Phe Ile Gly Phe Asp Gly Thr Glu Val
            260                 265                 270

Thr Val Lys Ala Val Ala Thr Asp Phe Gly Leu Thr Thr Gly Thr Asn
        275                 280                 285

Asn Leu Val Pro Phe Asn Leu Val Val Pro Thr Ser Glu Ile Thr Gln
290                 295                 300

Pro Ile Thr Ser Met Lys Leu Glu Val Val Thr His Lys Arg Gly Gly
305                 310                 315                 320

Thr Ala Gly Asp Pro Ile Ser Trp Thr Val Ser Gly Thr Leu Ala Val
                325                 330                 335

Thr Val His Gly Gly Asn Tyr Pro Gly Ala Leu Arg Pro Val Thr Leu
            340                 345                 350

Val Ala Tyr Glu Arg Val Ala Ala Gly Ser Val Val Thr Val Ala Gly
        355                 360                 365
```

-continued

```
Val Ser Asn Phe Glu Leu Ile Pro Asn Pro Glu Leu Ala Lys Asn Leu
    370             375             380

Val Thr Glu Tyr Gly Arg Phe Asp Pro Gly Ala Met Asn Tyr Thr Lys
385             390             395             400

Leu Ile Leu Ser Glu Arg Asp Arg Leu Gly Ile Lys Thr Val Trp Pro
            405             410             415

Thr Arg Glu Tyr Thr Asp Phe Arg Glu Tyr Phe Met Glu Val Ala Asp
            420             425             430

Leu Asn Ser Pro Leu Lys Ile Ala Gly Ala Phe Gly Phe Lys Asp Ile
        435             440             445

Ile Arg Ala Ile Arg Lys Ile Ala Val Pro Val Val Ser Thr Leu Phe
    450             455             460

Pro Pro Ala Ala Pro Leu Ala His Ala Ile Gly Glu Gly Val Asp Tyr
465             470             475             480

Leu Leu Gly Asp Glu Ala Gln Ala Ala Ser Gly Thr Ala Arg Ala Ala
            485             490             495

Ser Gly Lys Ala Arg Ala Ala Ser Gly Arg Ile Arg Gln Leu Thr Leu
            500             505             510

Ala Ala Asp Lys Gly
        515
```

INFECTIOUS BURSAL DISEASE (IBDV) VACCINE COMPOSITIONS

CROSS-REFERENCE TO RELATED APPLICATIONS

This application is a National Phase Application of International Application No. PCT/US2013/049453, filed Jul. 5, 2013, which claims priority to U.S. Patent Application No. 61/668,314, filed Jul. 5, 2012, which applications are incorporated herein fully by this reference.

REFERENCE TO SEQUENCE LISTING

The Sequence Listing submitted Jul. 30, 2013 as a text file named "26227_0024U2_Sequence_Listing.txt," created on Jul. 30, 2013, and having a size of 52,100 bytes is hereby incorporated by reference pursuant to 37 C.F.R. §1.52(e)(5).

BACKGROUND

Infectious bursal disease (also known as IBD, Gumboro Disease, Infectious Bursitis and Infectious Avian Nephrosis) is a highly contagious disease of young chickens caused by infectious bursal disease virus (IBDV), characterized by immunosuppression and mortality generally at 3 to 6 weeks of age. It is economically important to the poultry industry worldwide due to increased susceptibility to other diseases and negative interference with effective vaccination. In recent years, very virulent strains of IBDV (vvIBDV), causing severe mortality in chickens, have emerged in Europe, Latin America, South-East Asia, Africa and the Middle East. Infection is via the oro-fecal route, with affected birds excreting high levels of the virus for approximately 2 weeks after infection.

IBDV is a double stranded RNA virus that has a bi-segmented genome and belongs to the genus Avibirnavirus of family Birnaviridae. There are two distinct serotypes of the virus, but only serotype 1 viruses cause disease in poultry. At least six antigenic subtypes of IBDV serotype 1 have been identified by in vitro cross-neutralization assay. Viruses belonging to one of these antigenic subtypes are commonly known as variants, which were reported to break through high levels of maternal antibodies in commercial flocks, and cause immune suppression.

The IBDV genome consists of two segments, A and B, which are enclosed within a nonenveloped icosahedral capsid. The genome segment B (2.9 kb) encodes VP1, the putative viral RNA polymerase. The larger segment A (3.2 kb) encodes viral proteins VP2, VP3, VP4, and VP5. Among them, VP2 protein contains important neutralizing antigenic sites and elicits a protective immune response and most of the amino acid (AA) changes between antigenically different IBDVs are clustered in the hypervariable region of VP2. Thus, this hypervariable region of VP2 has been the target for the molecular techniques applied for IBDV detection and strain variation studies.

The IBDV capsid protein exhibits structural domains that show homology to those of the capsid proteins of some positive-sense single-stranded RNA viruses, such as the nodaviruses and tetraviruses, as well as the T=13 capsid shell protein of the Reoviridae. The T=13 shell of the IBDV capsid is formed by trimers of VP2, a protein generated by removal of the C-terminal domain from its precursor, pVP2. The trimming of pVP2 is performed on immature particles as part of the maturation process. The other major structural protein, VP3, is a multifunctional component lying under the T=13 shell that influences the inherent structural polymorphism of pVP2. The virus-encoded RNA-dependent RNA polymerase, VP1, is incorporated into the capsid through its association with VP3. VP3 also interacts extensively with the viral dsRNA genome.

Clinical disease is associated to bird age with the greatest bursal mass, which occurs between 3 and 6 weeks of age. The greatest bursal mass is mostly a result of a large population of maturing IgM-bearing B-lymphocytes (lymphoblasts), the main target of infection. Young birds at around two to eight weeks of age that have a highly active bursa of Fabricius are more susceptible to disease. Birds over eight weeks are more resistant to challenge and typically will not show clinical signs unless infected by highly virulent strains.

The poultry vaccine industry currently makes inactivated IBDV vaccines for administration to breeder chickens. Vaccinating parent breeder flocks produces maternal immunity in the chicks and protects them during the first few weeks of life from infectious bursal disease (IBD). In many cases, the vaccines for IBD are prepared in young chicks rather than eggs or cell culture because the quality and quantity of the antigen is considered to be superior. This is an expensive and time consuming process. Furthermore, animal use issues have increased the risk of losing this source of high quality IBDV antigens. Using antigens produced in eggs or cell culture could reduce the potency and efficacy of these vaccines and thus increase IBD related morbidity, mortality and the cost of poultry meat and egg production.

Therefore, what is needed in the art are safe and effective vaccines that can be practically produced to prevent IBDV.

DETAILED DESCRIPTION OF THE INVENTION

Figure 1:
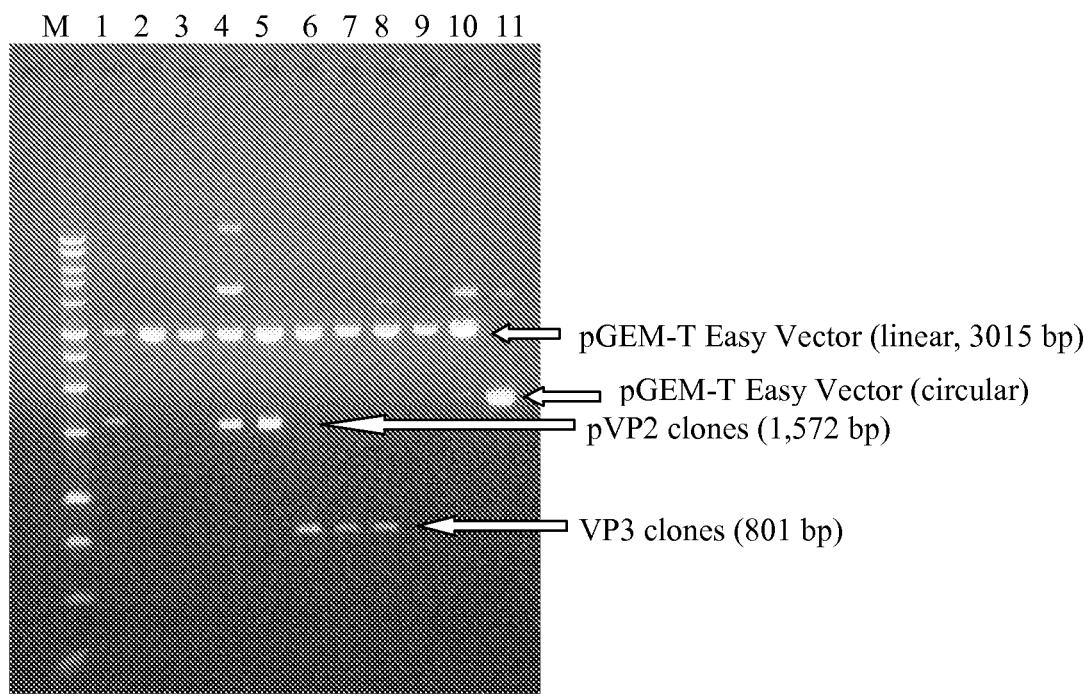
FIG. 1 shows IBDV pVP2 and VP3 clones excised from pGEM-T Easy vector using EcoRI. Lane M contains a molecular DNA ladder, lanes 1-5 contain pVP2 clones, lanes 6-9 contain VP3 clones, lane 10 contains a negative (no insert) control and lane 11 contains an un-cut negative control.

Before the present compounds, compositions, articles, devices, and/or methods are disclosed and described, it is to be understood that the aspects described below are not limited to specific synthetic methods or specific administration methods, as such may, of course, vary. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise.

"Optional" or "optionally" means that the subsequently described event or circumstance can or cannot occur, and that the description includes instances where the event or circumstance occurs and instances where it does not. For example, the phrase "optionally the composition can comprise a combination" means that the composition may comprise a combination of different molecules or may not include a combination such that the description includes both the combination and the absence of the combination (i.e., individual members of the combination).

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for a nucleic acid (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid (for example, a c-met nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, N.Y., 1998).

Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular VP2, VP3, or virus like particle (VLP) is disclosed and discussed and a number of modifications that can be made to a number of molecules including the VP2, VP3, or VLP are discussed, specifically contemplated is each and every combination and permutation of cancer gene or cooperation response gene and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The genome of IBDV consists of two segments of double-stranded RNA (Dobos 1979). The smaller genome segment encodes the RNA-dependent RNA polymerase, VP1 (von Einem 2004). The larger genome segment encodes a polyprotein that is self-cleaved by the viral encoded protease VP4 (Birghan 2000) to yield pVP2, VP3 and VP4 (Kibenge 1988). The pVP2 protein is further cleaved multiple times at the COOH terminus to yield the mature capsid protein VP2 (Galloux 2007). Trimers of the VP2 protein form a structure containing a base (B), shell (S) and projection (P) domain (Coulibaly 2010). The surface of the IBDV capsid is a single protein layer made up of 260 VP2 trimers and beneath this layer are at least 200 trimers of the VP3 protein (Coulibaly 2005). During viral replication, capsid formation may be initiated by a VP1-VP3 complex which interacts with VP2 trimers (Caston 2001; Moraver 2003; Lombardo 1999). However, in the absence of VP1, the molecular co-expression of pVP2 and VP3 also produced the correct capsid structure (Martinez 2000). The COOH terminal domain of pVP2 was essential for the assembly of the proteins into these virus-like particles (VLPs) (Ona 2004)

The antigenic variability among IBDV strains has been recognized for decades. It is determined by amino acids that constitute VP2 (Heine 1991; Eterradossi 1997; Eterradossi 1998). Specifically, amino acids in the P domain of VP2 are critical for the binding of neutralizing monoclonal antibodies (Letzel 2007). Neutralizing antibody escape mutant viruses had substitution mutations in the PBC, PDE and PHI domains (Vakharia 1994; Letzel 2007) Amino acid substitution mutations in the PBC and PDE domains also contributed to antigenic drift among IBDV strains (Schnitzler 1993).

As disclosed in Example 1, nucleotide sequences that encode the pVP2 proteins from a variant IBDV strain designated USA08MD34p and a classic IBDV strain designated Mo195 were produced using RT-PCR and cloned into a pGEM-T Easy vector. A nucleotide sequence that encodes the VP3 protein was also produced from the USA08MD34p viral genome using RT-PCR and cloned into a pGEM-T Easy vector. The VP3 and pVP2 clones were inserted into the pVL1393 Baculovirus transfer vector and sequenced to confirm their orientation to the promoter and to insure they contained uninterrupted open-reading-frames. Recombinant Baculoviruses were constructed by transfection in Sf9 cells. Three recombinant Baculoviruses were produced and contained the USA08MD34p-VP3, USA08MD34p-pVP2 or Mo195-pVP2 genomic sequences.

Virus-like particles (VLPs) were observed using transmission electron microscopy when the USA08MD34p-VP3 Baculovirus was co-inoculated into Sf9 cells with either of the pVP2 constructs. VLPs were also observed when the USA08MD34p-pVP2 and Mo195-pVP2 were co-expressed with USA08MD34p-VP3. These mosaic VLPs contained both classic and variant pVP2s. The USA08MD34p, Mo195 and mosaic VLPs were used to vaccinate chickens. They induced an IBDV specific antibody response that was detected by ELISA and virus-neutralizing antibodies were detected in vitro. Chickens vaccinated with the mosaic VLPs were protected from a virulent variant IBDV strain (V1) and a virulent classic IBDV strain (STC). The results indicate the mosaic VLPs maintained the antigenic integrity of the variant and classic viruses and have the potential to serve as a multivalent vaccine for use in breeder flocks.

VP2

Disclosed herein is a polyvalent VP2. By "VP2 of IBDV" and "VP3 of IBDV" is meant the full-length or substantially full-length IBDV viral protein, a fragment thereof, a fusion, or a viral protein with internal deletions. VP2 and VP3 can have the ability to form VLPs under conditions that favor VLP formation. Thus, VP2 can include pVP2/VPX, and VP2 wherein a portion of the C-terminal domain sufficient to form VLPs exists.

The polyvalent VP2 can be a trimer comprised of three VP2 monomers, or trimer forming fragments thereof. The term "polyvalent" refers to the VP2 trimer which is comprised of at least one VP2 monomer that is antigenically distinct from at least one other VP2 monomer in the VP2 trimer.

By "antigenically distinct" is meant that the monomers individually or as part of a trimer elicits a humoral/antibody response such that the monomers or trimers can be distinguished from other monomers or trimmers suing antibodies. An "antigen" or "antigenic" refers to a molecule containing one or more epitopes (either linear, conformational or both) that will stimulate a host's immune-system to make a humoral and/or cellular antigen-specific response.

"Immunogen" refers to a molecule that is able to provoke a humoral and/or cell-mediated immune response. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids Immunogens include, but is not limited to, polypeptides which include modifications, such as deletions, additions and substitutions (generally conservative in nature) as compared to a native sequence, so long as the protein maintains the ability to elicit an immunological response, as defined herein. Such modifications may be deliberate, as through site-directed mutagenesis, or may be accidental, such as through mutations of hosts which produce the antigens.

An "immunological response" or "immune response" to an antigen, immunogen or composition is the development in a subject of a humoral and/or a cellular immune response to an antigen present in the composition of interest.

It is understood herein that an "immune response" refers to any inflammatory, humoral, or cell-mediated response that occurs for the purpose of eliminating an antigen. Such responses can include, but are not limited to, antibody production, cytokine secretion, complement activity, and cytolytic activity. In one embodiment, the immune response is an antibody response.

A "humoral immune response" refers to an immune response mediated by antibody molecules, whereas a "cellular immune response" is one mediated by T-lymphocytes and/or other white blood cells. A "cellular immune response" can also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" refers to a composition that comprises an antigenic molecule where administration of the composition to a subject results in the development in the subject of a humoral and/or a cellular immune response to the antigenic molecule of interest.

The VP2 monomers, or trimer forming fragments thereof, can be selected from known IBDV strains, for example as provided herein, including natural segment A and B reassortments, variant strains, classic strains, very virulent strains, or from future discovered strains of IBDV. Examples of vvIBDV include but are not limited to UK661 (AJ878898), rA (GQ221682) and rB (GQ221683). Examples of variant viruses include but are not limited to Del-E (AJ878905), Del-A (Y1459), GLS (AJ878906), V1 (AF281235), GER (AF281228) and USAO2CA viruses (HQ441143-HQ441158). Examples of classic viruses include but are not limited to D78 (Y14962), Bursine (AJ878894), F52/70 (Y14958), Cu-1 ((AJ878886), V877 (AJ878882) and S706 (AJ878891). Examples of reassorted viruses include but are not limited to IBDV strain 02015.1 (GenBank accession numbers AJ879932 and AJ88090), CA-D495 (HQ441142), CA-K785 (HQ441143), and GX (AJ878907). Other examples of strains that could be used as the VP2 of IBDV include, but are not limited to UPM97/61 (AF247006), UPM94/273 (AF527039), OKYM (D49706), UK661 (X92760), IBDKS (L42284), D6948 (AF240686), BD3/99 (AF362776), Tasik94 (AF322444), Chinju (AF508176), HK46 (AF092943), SH95 (AF13474), Gx (AY 444873), SDH1 (AY323952) and T09 (AY099456), D78 (AF499929), Cu-1M (AF362771), P2 (X84034), CT (AJ310185), CEF94 (AF194428), PBG-98 (D00868), JD1 (AF321055), HZ-2 (AF321054), TAD Gumboro (CAI47764), Delvax, Gumboro LZD, IBDVAC, 89163, Farager 52/70 and Edgar (AF462026).

Any combination of VP2s can be utilized to form the trivalent VP2. Thus, provided herein are polyvalent VP2s comprising variant and/or classic and/or very virulent monomers. The VP2 monomer can comprise the identical amino acid sequences of a naturally occurring IBDV strain, modified amino acids not occurring naturally, fusions, or antigenic fragments thereof. Amino acid and nucleic acid sequences of VP2 monomers can be one or more of the sequences identified herein as SEQ ID Nos. herein for VP2 and/or one or more of the sequences described in Genbank, such as Accession Number AAV68391. For example, the polyvalent VP2 can comprise a VP2 monomer of IBDV variant strain USA08MD34p, or a VP2 monomer of IBDV classic strain Mo195. In another example, the polyvalent VP2 can comprise a VP2 monomer of IBDV variant strain USA08MD34p, or a VP2 monomer of IBDV classic strain Mo195 or a VP2 monomer from an IBDV strain which is not IBDV variant strain USA08MD34p and is not IBDV classic strain Mo195. The polyvalent VP2 can also comprise two VP2 monomers from IBDV variant strain USA08MD34p and one VP2 monomer from IBDV classic strain Mo195. In yet another example, the polyvalent VP2 can comprise one VP2 monomer from IBDV variant strain USA08MD34p and two VP2 monomers from IBDV classic strain Mo195. The polyvalent VP2 can also comprise two VP2 monomers of one IBDV and one an antigenically distinct IBDV monomer.

Thus, in one aspect, it is understood, that the polyvalent VP2 of IBDV can have the following formula: R1-R2-R3, wherein R1-R2-R3 are each VP2 monomers selected from the group consisting of IBDV strain USA08MD34p, classic strain Mo195, UPM97/61 (AF247006), UPM94/273 (AF527039), OKYM (D49706), UK661 (X92760), IBDKS (L42284), D6948 (AF240686), BD3/99 (AF362776), Tasik94 (AF322444), Chinju (AF508176), HK46 (AF092943), SH95 (AF13474), Gx (AY 444873), SDH1 (AY323952) and T09 (AY099456), D78 (AF499929), Cu-1M (AF362771), P2 (X84034), CT (AJ310185), CEF94 (AF194428), PBG-98 (D00868), JD1 (AF321055), HZ-2 (AF321054), TAD Gumboro, Delvax, Gumboro LZD, IBDVAC, 89163, Farager 52/70 and Edgar (AF462026); vvIBDV including but not limited to UK661 (AJ878898), rA (GQ221682) and rB (GQ221683); variant viruses including but not limited to Del-E (AJ878905), Del-A (Y1459), GLS (AJ878906), V1 (AF281235), GER (AF281228) and USAO2CA viruses (HQ441143-HQ441158); classic viruses including but not limited to D78 (Y14962), Bursine (AJ878894), F52/70 (Y14958), Cu-1 (AJ878886), V877 (AJ878882), and 5706 (AJ878891); and reassorted viruses including but not limited to CA-D495 (HQ441142), CA-K785 (HQ441143), IBDV strain 02015.1 (GenBank accession numbers AJ879932 and AJ88090), and GX (AJ878907). In one aspect, for example, at least one of R1, R2 and R3 is an antigenically distinct monomer from one or both of the other two monomers. In another aspect, at least one of R1, R2 and R3 is a VP2 monomer from a different strain of IBDV than the other monomers. Thus, provided herein are polyvalent VP2s comprising R1, R2 and R3 comprised of variant and/or classic and/or very virulent strain monomers. In yet another example, at least one of R1, R2 and R3 is a VP2 monomer of variant strain USA08MD34p and is an antigenically distinct monomer from at least one other monomer. In another example, at least one of R1, R2 and R3 is a VP2 monomer of IBDV classic strain Mo195 and is an antigenically distinct monomer from at least one other monomer. In another embodiment, at least one monomer is antigenically distinct from both other monomers.

Virus-Like Particles (VLPs)

In one aspect, disclosed herein are mosaic virus like particles (VLPs) comprising aVP2 as disclosed herein. As used herein, the terms "virus-like particle" or "VLP" refer to a nonreplicating, viral shell. VLPs are generally composed of one or more viral proteins, such as, but not limited to VP2s in the combinations disclosed herein, for example a combination of VP2 and VP3s. VLPs can form spontaneously upon recombinant expression of the protein in an appropriate expression system. VLPs, when administered to an animal, can be immunogenic and thus can cause a protective or therapeutic immune response in the animal. Methods for producing VLPs are generally known in the art and discussed more fully below. The presence of VLPs following recombinant expression of viral proteins can be detected using conventional techniques known in the art, such as by electron microscopy, biophysical characterization, and the like. See, e.g., Baker et al., Biophys. J. (1991) 60:1445-1456; Hagensee et al., J. Virol. (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

Also disclosed are mosaic virus like particles (VLPs). By "mosaic" is meant that the VLP comprises at least one VP2 trimer that is antigenicly distinct from at least one other VP2 trimer in the VLP. thus, for example disclosed herein are mosaic VLPs comprising a VP2 trimer from a different strain of IBDV than at least one VP2 trimers. The mosaic VLP can generate a polyvalent immune response. The VLP may can contain a multivalent VP2 and/or a monovalent VP2. A "monovalent VP2" means a VP2 trimer comprised of the same or substantially the same VP2 monomer. For example, the mosaic VLP can comprise two or more monovalent VP2 trimers and/or one or more polyvalent VP2 trimers. Mosaic VLPs comprising mixtures of monovalent and polyvalent VP2 trimers or exclusively monovalent or exclusively polyvalent VLP trimers are also disclosed herein.

Also disclosed herein are antigenically distinct trimers. Antigenically distinct trimers can be derived from or represented by different strains of IBDV, for example as provided herein. The VP2 trimers, or antigenic fragments thereof, whether polyvalent or monovalent, can be selected from known IBDV strains, such as those disclosed herein, or from additional strains of IBDV. The VP2 trimer can be selected for example from variant, classic, and very virulent strains. Thus, provided herein are mosaic VLPs comprised of VP2s from variant and/or classic and/or very virulent monomers. The VLP VP2 trimer can be polyvalent comprising two or more antigenically distinct or variant monomers and/or monomers having the identical amino acid sequences of a naturally occurring IBDV strain (i.e., the VLP can simultaneously comprise polyvalent and monovalent trimmers), can comprise modified amino acids not occurring naturally, can comprise fusions, or can comprise antigenic fragments thereof.

The amino acid sequence of VP2 monomers making up the VP2 trimers in the mosaic VLP can be one or more of the sequences identified herein as SEQ ID Nos. and/or one or more of the sequences described, for example, in Genbank Accession No. CAI47764. In another example, a polyvalent or monovalent VP2 trimer in the VLP can comprise a VP2 monomer of IBDV variant strain USA08MD34p, and/or a VP2 monomer of IBDV classic strain Mo195. In another example, the polyvalent or monovalent VP2 can comprise a VP2 monomer of IBDV variant strain USA08MD34p, a VP2 monomer of IBDV classic strain Mo195 and a VP2 monomer from an IBDV strain which is not IBDV variant strain USA08MD34p and is not IBDV classic strain Mo195. Examples of other strains that can be used as the VP2 of IBDV include, but are not limited to UPM97/61 (AF247006), UPM94/273 (AF527039), OKYM (D49706), UK661 (X92760), IBDKS (L42284), D6948 (AF240686), BD3/99 (AF362776), Tasik94 (AF322444), Chinju (AF508176), HK46 (AF092943), SH95 (AF13474), Gx (AY 444873), SDH1 (AY323952) and T09 (AY099456), D78 (AF499929), Cu-1M (AF362771), P2 (X84034), CT (AJ310185), CEF94 (AF194428), PBG-98 (D00868), JD1 (AF321055), HZ-2 (AF321054), TAD Gumboro, Delvax, Gumboro LZD, IBDVAC, 89163, Farager 52/70, and Edgar (AF462026). The VP2 monomers that make up the monovalent or polyvalent VP2 trimers, or fragments thereof, can be selected from known IBDV strains, for example as provided herein, or from future discovered strains of IBDV. Any combination of monovalent or polyvalent VP2s can be utilized to form the VLP. In addition, examples of the polyvalent VP2 trimers can, for example, comprise two VP2 monomers from IBDV variant strain USA08MD34p and one VP2 monomer from IBDV classic strain Mo195. In yet another example, the polyvalent VP2 trimer can comprise one VP2 monomer IBDV variant strain USA08MD34p and two VP2 monomers from IBDV classic strain Mo195. Likewise, the polyvalent VP2 trimer can, for example, comprise two VP2 monomers of one IBDV monomer and one IBDV from an antigenically distinct monomer.

The VLP can further comprise a VP3 or a fragment thereof, or any other protein or polypeptide allowing the assembly of antigenic or immunogenic VP2 trimers as a VLP of the invention. The VLP can also comprise other IBDV proteins such a VP1. Proteins from viruses having similar functionality to VP3 can also comprise the VLPs of this invention.

Antibodies

Disclosed herein are methods for the generation of antibodies that specifically recognize the mosaics and fragments of the VP2s and VLPs disclosed herein. These antibodies, whether polyclonal, monoclonal, chimeric, or antibody fragments would recognize and target the mosaics and fragments disclosed herein. Antibodies to any of the substances on the list of mosaics can also be used as "passive vaccines" for the direct immunotherapeutic targeting of IBDV of the corresponding VP2s or VLPs disclosed herein in vivo. It is understood that disclosed are any antibody including monoclonal, polyclonal, or chimerized for example, binding any fragment of any of the compositions disclosed herein.

The antibodies provided herein are capable of neutralizing IBDV of other closely related species to IBDV. The provided antibodies can be delivered directly, such as through needle injection, for example, to treat IBDV infections. The provided antibodies can be delivered non-invasively, such as intranasally, for example. The antibodies can also be encapsulated, for example into lipsomes, microspheres, or other transfection enhancement agents, for improved delivery into the cells to maximize the treatment efficiency. The gene sequences encoding the provided antibodies, or their fragments such as Fab fragments, can further be cloned into genetic vectors, such as plasmid or viral vectors, for example, and delivered into the hosts for endogenouse expression of the antibodies for treatment of IBDV.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as Fv, sFv, F(ab')2, Fab', Fab and the like, including hybrid fragments. Thus, fragments of the antibodies that retain the ability to bind their specific antigens are provided. For example, fragments of antibodies which maintain EFn binding activity are included within the meaning of the term "antibody or fragment thereof" Such antibodies and fragments can be made by techniques known in the art and can be screened for specificity and activity using general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human Antibodies

The disclosed human antibodies can be prepared using any technique. Examples of techniques for human monoclonal antibody production include those described by Cole et al. Human antibodies (and fragments thereof) can also be produced using phage display libraries.

The disclosed human antibodies can also be obtained from transgenic animals. For example, transgenic, mutant mice that are capable of producing a full repertoire of human antibodies, in response to immunization. Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody Disclosed herein are antigens expressed in baculovirus. The advantages to this system include ease of generation, high levels of expression, and post-translational modifications that are highly similar to those seen in mammalian systems. The antigen is produced by inserting a gene fragment in-frame between the signal sequence and the mature protein domain of a nucleotide sequence.

Nucleic Acids and Cells

It is understood and herein contemplated that in one aspect the VP2, VP3, and/or VLPs are present in the disclosed compositions as nucleic acids. The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof The nucleic acids, such as SEQ ID NOS 1-24, as described herein, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 3rd Edition (Cold Spring Harbor Laboratory Press, Cold Spring Harbor, N.Y., 2001) Chapters 5, 6) to purely synthetic methods, for example, by the cyanoethyl phosphoramidite method using a Milligen or Beckman System 1Plus DNA synthesizer. Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

The compositions disclosed herein can be produced as described herein and can be prepared using standard recombinant techniques. Polynucleotides encoding the VLP-forming protein(s) are introduced into a host cell and, when the proteins are expressed in the cell, they can assemble into the VP2s or VLPs.

Polynucleotide sequences coding for proteins or polypeptides, including structural and/or antigen polypeptides, including modified antigenic polypeptides) that form and/or are incorporated into the VP2s and VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

Any of the proteins used in the VP2s and VLPs described herein may be hybrid (or chimeric) proteins, referred to herein as mosaics. It will be apparent that all or parts of the polypeptides can be replaced with sequences from other viruses and/or sequences from other IBDV strains so long as the sequence does not prevent the formation of VP2 trimers and/or VLPs.

Preferably, the sequences employed to form the VP2s and VLPs disclosed herein can exhibit between about 60% to 80% (or any value therebetween including 61%, 62%, 63%, 64%, 65%, 66%, 67%, 68%, 69%, 70%, 71%, 72%, 73%, 74%, 75%, 76%, 77%, 78% and 79%) sequence identity to a naturally occurring IBDV polynucleotide sequence and more preferably the sequences exhibit between about 80% and 100% (or any value therebetween including 81%, 82%, 83%, 84%, 85%, 86%, 87%, 88%, 89%, 90%, 91%, 92%, 93%, 94%, 95%, 96%, 97%, 98% and 99%) sequence identity to a naturally occurring polynucleotide sequence.

Any of the sequences described herein may further include additional sequences. For example, to further to enhance vaccine potency, hybrid molecules are expressed and incorporated into the sub-viral structure. These hybrid molecules are generated by linking for example, at the DNA level, the sequences coding for the VP2s or VP3s with sequences coding for an adjuvant or immuno-regulatory moiety. The incorporation of one or more polypeptide immunomodulatory polypeptides (e.g., adjuvants described herein) into the sequences described herein into the VP2s and VLPs can enhance potency and therefore reduces the amount of antigen required for stimulating a protective immune response. Alternatively, as described below, one or more additional molecules (polypeptide or small molecules)

may be included in the VP2s and VLPs after production of the composition from the sequences described herein.

These sub-viral structures do not contain infectious viral nucleic acids and they are not infectious eliminating the need for chemical inactivation. Absence of chemical treatment preserves native epitopes and protein conformations enhancing the immunogenic characteristics of the vaccine.

The sequences described herein can be operably linked to each other in any combination. For example, one or more sequences may be expressed from the same promoter and/or from different promoters. As described below, sequences may be included on one or more vectors.

Expression Vectors

Once the constructs comprising the sequences encoding the polypeptide(s) desired to be incorporated into the VP2s and VLPs have been synthesized, they can be cloned into any suitable vector or replicon for expression. Numerous cloning vectors are known to those of skill in the art, and one having ordinary skill in the art can readily select appropriate vectors and control elements for any given host cell type in view of the teachings of the present specification and information known in the art about expression. See, generally, Ausubel et al, supra or Sambrook et al, supra.

Non-limiting examples of vectors that can be used to express sequences that assembly into VP2s and VLPs as described herein include viral-based vectors (e.g., retrovirus, adenovirus, adeno-associated virus, lentivirus), baculovirus vectors (see Examples), plasmid vectors, non-viral vectors, mammalians vectors, mammalian artificial chromosomes (e.g., liposomes, particulate carriers, etc.) and combinations thereof.

The expression vector(s) typically contain(s) coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., Mamm. Genome 7(8):563-574, 1996; Kozak, M., Biochimie 76(9): 815-821, 1994; Kozak, M., J Cell Biol 108(2):229-241, 1989; Kozak, M., and Shatkin, A. J., Methods Enzymol 60:360-375, 1979).

It will be apparent that one or more vectors may contain one or more sequences encoding proteins to be incorporated into the VP2s and VLPs. For example, a single vector may carry sequences encoding all the proteins found in the composition. Alternatively, multiple vectors may be used (e.g., multiple constructs, each encoding a single polypeptide-encoding sequence or multiple constructs, each encoding one or more polypeptide-encoding sequences). In embodiments in which a single vector comprises multiple polypeptide-encoding sequences, the sequences may be operably linked to the same or different transcriptional control elements (e.g., promoters) within the same vector. Furthermore, vectors may contain additional gene expression controlling sequences including chromatin opening elements which prevent transgene silencing and confer consistent, stable and high level of gene expression, irrespective of the chromosomal integration site. These are DNA sequence motifs located in proximity of house-keeping genes, which in the vectors create a transcriptionally active open chromatin environment around the integrated transgene, maximizing transcription and protein expression, irrespective of the position of the transgene in the chromosome.

In addition, one or more sequences encoding non-IBDV proteins may be expressed and incorporated into the VP2s and VLPs, including, but not limited to, sequences comprising and/or encoding immunomodulatory molecules (e.g., adjuvants described below), for example, immunomodulating oligonucleotides (e.g., CpGs), cytokines, detoxified bacterial toxins and the like.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

Peptides

By "particle-forming polypeptide" derived from a particular viral protein is meant a full-length viral protein or a fragment thereof, a fusion of a viral protein, or a viral protein with internal deletions, which has the ability to form VLPs under conditions that favor VLP formation. Accordingly, the polypeptide may comprise the full-length sequence, fusions, fragments, truncated and partial sequences, as well as analogs and precursor forms of the reference molecule. Examples are disclosed herein, but can include VP2 proteins alone, or in combination with VP3 proteins, thereby forming VLPs. Thus, a "particle-forming polypeptide" derived from VP2 of IBDV includes, but is not limited to, full-length or near full-length viral protein, a fragment thereof, a fusion, or a viral protein with internal deletions, which has the ability to form VLPs under conditions that favor VLP formation. "Particle-forming polypeptide" also includes, but is not limited to, deletions, additions and substitutions to the sequence, so long as the polypeptide retains the ability to form a VLP. "Particle-forming polypeptide" also includes, but is not limited to, natural variations of the specified polypeptide since variations in coat proteins often occur between viral isolates as well as deletions, additions and substitutions that do not naturally occur in the reference protein, so long as the protein retains the ability to form a VLP.

Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids.

"Peptide" as used herein refers to any peptide, oligopeptide, polypeptide, gene product, expression product, or protein. For example, a peptide can be a receptor. A polypeptide is comprised of consecutive amino acids. The term "polypeptide" encompasses naturally occurring or synthetic molecules.

In addition, as used herein, the term "peptide" or "polypeptide" refers to amino acids joined to each other by peptide bonds or modified peptide bonds, e.g., peptide isosteres, etc. and may contain modified amino acids other than the 20 gene-encoded amino acids. Polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, the term "amino acid sequence" refers to a list of abbreviations, letters, characters or words representing amino acid residues.

Pharmaceutical Compositions

Polyvalent compositions produced as described herein can be used to elicit an immune response when administered to a subject. As discussed above, the compositions can comprise a variety of antigens (e.g., one or more modified IBVD antigens from one or more strains or isolates). Purified polyvalent compositions can be administered to a vertebrate subject, usually in the form of vaccine compositions. Combination vaccines may also be used, where such vaccines contain, for example, other subunit proteins derived from IBDV or other organisms and/or gene delivery vaccines encoding such antigens.

In one aspect, disclosed herein are vaccines comprising the VP2s and/or VLPs disclosed herein. It is understood that the disclosed vaccines can be therapeutic or prophylactic. Thus, for example, disclosed herein are vaccines comprising VP2s or VLps comprising a polyvalent or monovalent VP2 trimer in the VLP. For example, disclosed herein are vaccines wherein the VLP can comprise one or more VP2 monomers of IBDV variant strain USA08MD34p, and/or one or more VP2 monomer of IBDV classic strain Mo195. In another example, the vaccine can comprise VP2s or VLPs comprising polyvalent or monovalent VP2 trimers wherein the trimer comprises at least one VP2 monomer of IBDV selected from the group consisting of variant strain USA08MD34p, a VP2 monomer of IBDV classic strain Mo195 and a VP2 monomer from an IBDV strain which is not IBDV variant strain USA08MD34p and is not IBDV classic strain Mo195. In another example, the vaccine can comprise VP2s or VLPs comprising polyvalent or monovalent VP2 trimers wherein the trimer comprises at least one or more VP2 monomer of IBDV selected from the group consisting of USA08MD34p, Mo195, UPM97/61 (AF247006), UPM94/273 (AF527039), OKYM (D49706), UK661 (X92760), IBDKS (L42284), D6948 (AF240686), BD3/99 (AF362776), Tasik94 (AF322444), Chinju (AF508176), HK46 (AF092943), SH95 (AF13474), Gx (AY 444873), SDH1 (AY323952) and T09 (AY099456), D78 (AF499929), Cu-1M (AF362771), P2 (X84034), CT (AJ310185), CEF94 (AF194428), PBG-98 (D00868), JD1 (AF321055), HZ-2 (AF321054), TAD Gumboro, Delvax, Gumboro LZD, IBDVAC, 89163, Farager 52/70, and Edgar (AF462026).

Therefore, disclosed herein are compositions comprising the polyvalent VP2s and/or VLPs described herein, along with a pharmaceutically acceptable carrier. VLPs and VP2s produced as described herein can be used to elicit an immune response when administered to a subject. Purified VLPs or VP2s can be administered to a subject, usually in the form of vaccine compositions. VP2/VLP immune-stimulating (or vaccine) compositions can include various excipients, adjuvants, carriers, auxiliary substances, modulating agents, and the like. The immune stimulating compositions can include an amount of the VP2/antigen or VLP/antigen sufficient to mount an immunological response. An appropriate effective amount can be determined by one of skill in the art.

By an "effective amount" of a compound as provided herein is meant a sufficient amount of the compound to provide the desired effect. For example, an effective amount of a compound can refer to a sufficient amount of the compound to generate an immune response. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

Typically, an effective amount will fall in a relatively broad range that can be determined through routine trials and will generally be an amount on the order of about 0.1 µg to about 10 (or more) µg, more preferably about 1 µg to about 300 µg, even more preferably 25 µg to 50 µg of VP2/antigen or VLP/antigen. Sub-viral structure vaccines are purified from the cell culture medium and formulated with the appropriate buffers and additives, such as a) preservatives or antibiotics; b) stabilizers, including proteins or organic compounds; c) adjuvants or immuno-modulators for enhancing potency and modulating immune responses (humoral and cellular) to the vaccine; or d) molecules that enhance presentation of vaccine antigens to specifics cell of the immune system. This vaccine can be prepared in a freeze-dried (lyophilized) form in order to provide for appropriate storage and maximize the shelf-life of the preparation. This will allow for stock piling of vaccine for prolonged periods of time maintaining immunogenicity, potency and efficacy.

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Pharmaceutically Acceptable Carriers

The compositions, including antibodies, can be used therapeutically in combination with a pharmaceutically acceptable carrier.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Additionally, these carriers can function as immunostimulating agents ("adjuvants"). Exemplary adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detoxu); (3) saponin adjuvants, such as Stimulom™. (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition. Muramyl peptides include, but are not limited to, N-acetyl-muramyl-L-threonyl-D-isoglutamine (thr-MDP), N-acetyl-normuramyl-L-alanyl-D-isogluatme (nor-MDP), N-acetylmuramyl-L-alanyl-D-isogluatminyl-L-alanine-2-(1'-2'-dipalmitoyl-s-n-glycero-3-huydroxyphosphoryloxy)-ethylamine (MTP-PE), etc.

Examples of suitable immunomodulatory molecules for use herein include adjuvants described above and the following: IL-1 and IL-2 (Karupiah et al. (1990) J. Immunology 144:290-298, Weber et al. (1987) J. Exp. Med. 166: 1716-1733, Gansbacher et al. (1990) J. Exp. Med. 172:1217-1224, and U.S. Pat. No. 4,738,927-); IL-3 and IL-4 (Tepper et al. (1989) Cell 57:503-512, Golumbek et al. (1991) Science 254:713-716, and U.S. Pat. No. 5,017,691); IL-5 and IL-6 (Brakenhof et al. (1987) J. Immunol. 139:4116-4121, and International Publication No. WO 90/06370); IL-7 (U.S. Pat. No. 4,965,195); IL-8, IL-9, IL-10, IL-11, IL-12, and IL-13 (Cytokine Bulletin, Summer 1994); IL-14 and IL-15; alpha interferon (Finter et al. (1991) Drugs 42:749-765, U.S. Pat. Nos. 4,892,743 and 4,966,843, International Publication No. WO 85/02862, Nagata et al. (1980) Nature 284:316-320, Familletti et al. (1981) Methods in Enz. 78:387-394, Twu et al. (1989) Proc. Natl. Acad. Sci. USA 86:2046-2050, and Faktor et al. (1990) Oncogene 5:867-872); .beta.-interferon (Seif et al. (1991) J. Virol. 65:664-671); γ-interferons (Watanabe et al. (1989) Proc. Natl. Acad. Sci. USA 86:9456-9460, Gansbacher et al. (1990) Cancer Research 50:7820-7825, Maio et al. (1989) Can. Immunol. Immunother. 30:34-42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) J. Immunology 144:942-951); CD3 (Krissanen et al. (1987) Immunogenetics 26:258-266); ICAM-1 (Altman et al. (1989) Nature 338:512-514, Simmons et al. (1988) Nature 331:624-627); ICAM-2, LFA-1, LFA-3 (Wallner et al. (1987) J. Exp. Med. 166:923-932); MHC class I molecules, MHC class II molecules, B7.1-.beta.2-microglobulin (Pames et al. (1981) Proc. Natl. Acad. Sci. USA 78:2253-2257); chaperones such as calnexin; and MHC-linked transporter proteins or analogs thereof (Powis et al. (1991) Nature 354:528-531) Immunomodulatory factors canalso be agonists, antagonists, or ligands for these molecules. For example, soluble forms of receptors can often behave as antagonists for these types of factors, as can mutated forms of the factors themselves.

Administration

The VP2s, VLPs and compositions comprising them can be administered to a subject by any mode of delivery, including, for example, by parenteral injection (e.g. subcutaneously, intraperitoneally, intravenously, intramuscularly, or to the interstitial space of a tissue), or by rectal, oral (e.g. tablet, spray), vaginal, topical, transdermal (e.g. see WO99/27961) or transcutaneous (e.g. see WO02/074244 and WO02/064162), intranasal (e.g. see WO03/028760), ocular, aural, pulmonary or other mucosal administration. In one example, the composition is administered in a mist. Multiple doses can be administered by the same or different routes.

The VLPs (and VLP-containing compositions) can be administered prior to, concurrent with, or subsequent to delivery of other vaccines. Also, the site of VLP administration may be the same or different as other vaccine compositions that are being administered.

Dosage treatment with the VLP composition can be a single dose schedule or a multiple dose schedule. A multiple dose schedule is one in which a primary course of vaccination may be with 1-10 separate doses, followed by other doses given at subsequent time intervals, chosen to maintain and/or reinforce the immune response. The dosage regimen will also, at least in part, be determined by the potency of the modality, the vaccine delivery employed, the need of the subject and be dependent on the judgment of the practitioner. In one example, two doses are given, and are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more days apart. In one embodiment, the first two doses are given 7-10 days apart. In another embodiment the doses can be 3-4 weeks apart.

The vaccines disclosed herein can provide antibody titers of 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000, 10500, 11000, 11500, and 12000, and titers of 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000, 10500, 11000, 11500, and 12000, 2, 4, 6, 8, 10, 12, 14, 16, 18, and 20 weeks post-immunization following 1, 2, 3, 4, 5, or more immunizations.

The dose of VLP or VP2 administered can vary, depending on the age or condition of the subject. Typically, for a VLP, the dose is between 15-75 µg, and more specifically between 25-50 µg.

Kits

Disclosed herein are kits comprising the one or more of the compositions, including, but not limited to, the polyvalent VP2s, VLPs, nucleic acids, antibodies, or cells disclosed herein.

Aquabirnavirus

Infectious pancreatic necrosis virus is the causative agent of infectious pancreatic necrosis disease (IPN) that infects salmonids and remains a serious problem in the aquaculture industry. IPN is especially contagious and destructive to juvenile trout and salmon. Highly virulent strains may cause greater than 70% mortality in hatchery stocks over a period of two months. This disease is especially destructive in salmonid eggs and fingerlings. Survivors of infection can remain lifelong asymptomatic carriers and serve as reservoirs of infection, shedding virus in their feces and reproductive products. Losses due to IPNV on salmon smoltification have been estimated at 5%. Economic losses due to IPNV in aquaculture were estimated to be over 560 million in 1996. This has been reduced as vaccines for salmonids became available based on killed virus or recombinantly produced viral peptides. However, these vaccines are not completely effective and can only be used in fairly large fish due to the reliance on injection for vaccination.

Polyvalent VP2s and mosaic VLPs, and compositions of the invention can also be from members of the aquabirnavirus genus of birnavirus family. In particular, the species infectious pancreatic necrosis virus (IPNV) can be used to form polyvalent VP2s and mosaic VLPs as described herein and exemplified for IBDV.

Production of VP2s and VLPs for IPNV can be accomplished using the techniques described herein for IBDV utilizing sequences, for example, of pVP2 (ACY35990) and VP3 (AAM90322) from IPNV and other aquabirnaviruses. In particular, the IPNV sequences can be substituted for the IBDV sequences set forth in the examples. The IPNV pVP2 gene can be amplified using RT-PCR and specific primers for that gene. The IPNV VP3 gene can also be amplified using RT-PCR and specific primers for its sequence. The amplified genes can then be ligated into a Baculovirus expression vector (pVL1392) and then used to transfect Baculoviruses Recombinant Baculoviruses containing either the pVP2 or VP3 genes from IPNV can be used to express their respective proteins. Co-expression of the pVP2 and VP3 proteins in insect cells can be conducted to produce VLPs. The VLPs can be administered to fish for prevention of the diseases associated with IPNV in fish. Examples of such administration can be found, for example, in US 2010/0092521 A1, herein incorporated by reference in its entirety. The VLPs can also be used to detect the presence of IPNV in a sample, as set forth for IBDV herein.

"Aquatic animal", as used herein, includes any multicellular organism that lives in water, typically fish. Preferably, said aquatic animal is an animal belonging to a fish species reared by aquaculture. Illustrative examples of said aquatic animals include teleost fish, such as vertebrate fish, e.g. salmonids (e.g., rainbow trout, salmon, etc.), carp, turbot, gilthead sea bream, sea bass, etc.

Disclosed herein is a method of eliciting an immune response against IPNV in a subject comprising administering to the subject an IPNV polyvalent VP2, and/or mosaic VLP, composition, or nucleic acid encoding the VP2/VLP. Another aspect of the invention also relates to a vaccine comprising IPNV polyvalent VP2 and/mosaic VLPs. The vaccine can be used to protect aquatic animals that can be infected by aquatic animal pathogens. In a particular embodiment, said pathogens are pathogens of aquatic animals reared in aquaculture installations. The vaccine of the invention can be administered by any appropriate route of administration that results in an immune response to protect against the pathogen in question, for which the vaccine will be formulated in a manner that is suitable for the chosen route of administration. Although the vaccine of the invention can be administered orally, intramuscularly, by particle bombardment or by spraying using conventional methods (U.S. Pat. No. 5,780,448) for the simultaneous immunisation of a large number of aquatic animals, another method is to submerge said aquatic animals in a solution comprising the vaccine of the invention. To do this, the vaccine of the invention can be prepared in the form of an aqueous solution or suspension, in a pharmaceutically acceptable vehicle, such as saline solution, phosphate buffered saline (PBS), or any other pharmaceutically acceptable vehicle.

The vaccine of the invention can be prepared using conventional methods known by a person skilled in the art. In a particular embodiment, said vaccine can be prepared using the mixture, if applicable, of a vector of the invention, optionally having one or more adjuvants and/or pharmaceutically acceptable vehicles.

Furthermore, another aspect of the invention relates to a method for simultaneously administering a vaccine to a plurality of aquatic animals (mass vaccination) that comprises the immersion of a plurality of aquatic animals in a bath containing the vaccine and the sonication of the bath containing said aquatic animals and said vaccine. Other methods of IPNV vaccine administration can be found, for example, in US 2007/0248623 A1, herein incorporated by reference in its entirety for its teaching concerning IPNV.

Methods

Immune Response

Disclosed herein are methods of eliciting an immune response against IBDV in a subject comprising administering to the animal one or more VP2s or VLPs, or a composition or nucleic acid thereof. The immune response can be considered to be efficacious if the desired result is obtained.

By "efficacy," "efficacious," or "sufficiency" means the ability to function as intended. For example, an "efficacious" immune response is a response that is able to afford the subject an acceptable degree of immune protection from the immunizing antigen. Thus, the present methods disclose methods of assessing the ability of an immune response to provide immune protection against future antigenic encounter. Traditionally, such methods involve antigenic challenge. It is understood that the present methods provide an alternative means to achieve the goal of antigenic challenge and can be used separately or in conjunction with a challenge to determine efficacy or sufficiency.

The term "sufficient or effective immune response" is used to describe an immune response of a large enough magnitude to provide an acceptable immune protection to the subject against future antigen encounter. It is understood that immune protection does not necessarily mean prevention of future antigenic encounter (e.g., infection), nor is it limited to a lack of any pathogenic symptoms "Immune protection" means a prevention of the full onset of a pathogenic condition. Thus, in one embodiment, a "sufficient immune response" is a response that reduces the symptoms, magnitude, or duration of an infection or other disease condition when compared with an appropriate control. The control can be a subject that is exposed to an antigen before or without a sufficient immune response.

For example, "protective against" can mean that the subject is prevented from acquiring one or more symptoms associated with IBD virus infection, or from having any negative response when exposed to the virus, or is prevented from dying from the disease, or dying from the disease within a given time period, such as 1, 2, 3, 4, 5, 6, 7, 8, 9, 10, 11, 12, 13, 14, 15, or 16 weeks, or 5, 6, 7, 8, 9, 10, 11, or 12 months, or any amount of time in between.

For example, the survival rate of a group of subjects to which the molecules are administered can have a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% improvement in mortality rate. By "mortality rate" is meant that the subject has an increased lifespan. For example, if 100 broilers are given a vaccine (as disclosed herein) which immunizes them against IBDV, and 95% of them survive past a given time, such as 3-4 weeks, then the vaccine is considered to impart a 95% survival rate.

In another example, the subject (such as a parental line, broiler or layer) can be administered a virulent IBDV to monitor the immune response. As outlined above, this can increase the lifespan of the subject by a given time period. The virulent IBDV can also be administered to a subject that has not received the vaccine (a control), and both can be monitored to determine the effectiveness of the vaccine. The immune response for both can be measured either by observation of the onset of symptoms of IBDV, or by monitoring the immune response of the subjects.

As outlined herein, there are multiple strains of IBDV, and any of these strains can be given to a subject who has been vaccinated, and/or a control, in order to monitor the effectiveness of the vaccine. Examples of such strains include, but are not limited to, the V1 variant virus and STC classic virus strain.

Disclosed herein are methods of reducing immunosuppression in a subject comprising the steps of: providing a composition as disclosed herein, such as one comprising a VP2s or VLPs, and administering said composition to the subject. As outlined herein, the subject can be an avian, such as a chicken. By "reducing immunosuppression" is meant that the amount of immunosuppression in a given subject after vaccination is less than that in an unvaccinated subject. By "immunosuppression" is meant suppression of the immune systems by IBDV. The amount that immunosuppression is reduced in a given individual subject can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% when compared to a control.

Also disclosed is a method of reducing death in a subject comprising the steps of: providing a composition comprising a VP2s or VLPs, as described herein, and administering said composition to the subject. As discussed herein, by "reducing death" is meant increasing survival rate of the subject as compared to a control.

As used herein, the term "treatment" refers to the medical management of a subject with the intent to produce a therapy, cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The treatment can be any reduction from native levels and can be but is not limited to the complete ablation of the disease, condition, or the symptoms of the disease or condition. Thus, the reduction can be a 10, 20, 30, 40, 50, 60, 70, 80, 90, 100%, or any amount of reduction in between as compared to native or control levels.

By "treat" is meant to administer a compound or molecule to a subject, such as an animal (for example, a chicken), that has a condition or disease, such as IBDV, an increased susceptibility for developing such a disease, in order to prevent or delay a worsening of the effects of the disease or condition, or to partially or fully reverse the effects of the disease. To "treat" can also refer to non-pharmacological methods of preventing or delaying a worsening of the effects of the disease or condition, or to partially or fully reversing the effects of the disease. For example, "treat" is meant to mean a course of action to prevent or delay a worsening of the effects of the disease or condition, or to partially or fully reverse the effects of the disease other than by administering a compound.

By "prevent" is meant to minimize the chance that a subject who has a susceptibility for developing disease, such as IBDV induced disease, will develop a such a disease, or one or more symptoms associated with the disease.

By "subject" is meant any member of the subphylum chordata, and in particular the ayes class, although the methods and compositions disclosed herein are relevant to any animal that can for example contract IBDV (infectious bursal disease virus) or IPNV (infectious pancreatic necrosis virus). Examples of members of the ayes class include, but are not limited to, those found in the superorder palaeognathae:struthioniformes (ostriches, emus, kiwis, and allies), and tinamiformes (tinamous). Also included is the superorder neognathae, which includes anseriformes (waterfowl), galliformes (fowl, including chickens, ducks, geese, guinea, quail, grouse, pheasant and turkeys), charadriiformes (gulls, button-quails, plovers and allies), gaviiformes (loons), podicipediformes (grebes), procellariiformes (albatrosses, petrels, and allies), sphenisciformes (penguins), pelecaniformes (pelicans and allies), phaethontiformes (tropicbirds), ciconiiformes (storks and allies), cathartiformes (New World vultures), phoenicopteriformes (flamingos), falconiformes (falcons, eagles, hawks and allies), gruiformes (cranes and allies), pteroclidiformes (sandgrouse), columbiformes (doves and pigeons), psittaciformes (parrots and allies), cuculiformes (cuckoos and turacos), opisthocomiformes (hoatzin), strigiformes (owls), caprimulgiformes (nightjars and allies), apodiformes (swifts and hummingbirds), coraciiformes (kingfishers and allies), piciformes (woodpeckers and allies), trogoniformes (trogons), coliiformes (mousebirds), and passeriformes (passerines). The term does not denote a particular age. Thus, both adult and newborn individuals are intended to be covered. The system described above is intended for any animal capable of contracting IBDV.

Diagnostics

The VLPs disclosed herein can be used as a diagnostic tool to detect, for example IBDV or IPNV antibodies in a sample.

As used herein, the term "diagnosed" means having been subjected to an examination by a person of skill, for example, a physician, and found to have a condition that can be diagnosed or treated by the compounds, compositions, or methods disclosed herein. For example, "diagnosed with IBDV" means having been subjected to an examination by a person of skill, for example, a veterinarian, and found to have a condition that can be diagnosed or treated by one or more of the compositions described herein.

Examples of diagnostic tools include but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners.

As seen in Example 2, the VLP antigens can react with serum antibodies to IBDV and produce a positive result in the ELISA. Chicken serum samples from birds not exposed to IBDV were negative in the assay. The results indicate that VLP antigens can be used in the ELISA to detect antibodies to IBDV strains.

Thus, this invention provides a method of detecting or determining the presence of IBDV or IBDV in a sample comprising contacting a VLP of this invention with an antibody containing sample from a patient and detecting the presence and/or absence of binding between the VLP and the antibodies in the sample.

Measuring Responsiveness

The immune response can be measured in a subject to assess the viability or usefulness of the composition, or to determine if multiple doses need to be administered. Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations.

The use of immunoassays to detect a specific protein can involve the separation of the proteins by electrophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121:321349 (1964), each of which is herein incorporated by reference in its entirety for teachings regarding electrophoresis methods. Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an protein expression profile assay as contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, 1251). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis-I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., 32P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialized chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include color coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the PROTEINCHIP® array (Ciphergen, Fremont, Calif.), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

The methods disclosed herein comprise assessing/measuring the efficacy or sufficiency of an immune response to a selected antigen in a subject. The disclosed methods utilize tissue samples from the subject to provide the basis for assessment. Such tissue samples can include, but are not limited to, blood (including peripheral blood and peripheral blood mononuclear cells), tissue biopsy samples (e.g., spleen, liver, bone marrow, thymus, lung, kidney, brain, salivary glands, skin, lymph nodes, and intestinal tract), and specimens acquired by pulmonary lavage (e.g., bronchoalveolar lavage (BAL)). Thus it is understood that the tissue sample can be from both lymphoid and non-lymphoid tissue. Examples of non-lymphoid tissue include but are not limited to lung, liver, kidney, and gut. Lymphoid tissue includes both primary and secondary lymphoid organs such as the spleen, bone marrow, thymus, and lymph nodes.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Mosaic Virus-Like-Particle Vaccine Protects Against Classic and Variant Infectious Bursal Disease Viruses Nucleotide sequences that encode the pVP2 proteins from a variant IBDV strain designated USA08MD34p and a classic IBDV strain designated Mo195 were produced using RT-PCR and cloned into a pGEM-T Easy vector. A nucleotide sequence that encodes the VP3 protein was also produced from the USA08MD34p viral genome using RT-PCR and cloned into a pGEM-T Easy vector. The VP3 and pVP2 clones were inserted into the pVL1393 Baculovirus transfer vector and sequenced to confirm their orientation to the promoter and to insure they contained uninterrupted open-reading-frames. Recombinant Baculoviruses were constructed by transfection in Sf9 cells. Three recombinant Baculoviruses were produced and contained the USA08MD34p-VP3, USA08MD34p-pVP2 or Mo195-pVP2 genomic sequences. Virus-like particles (VLPs) were observed using transmission electron microscopy when the USA08MD34p-VP3 Baculovirus was co-inoculated into Sf9 cells with either of the pVP2 constructs. VLPs were also observed when the USA08MD34p-pVP2 and Mo195-pVP2 were co-expressed with USA08MD34p-VP3. These mosaic VLPs contained both classic and variant pVP2s. The USA08MD34p, Mo195 and mosaic VLPs were used to vaccinate chickens. They induced an IBDV specific antibody response that was detected by ELISA and virus-neutralizing antibodies were detected in vitro. Chickens vaccinated with the mosaic VLPs were protected from a virulent variant IBDV strain (V1) and a virulent classic IBDV strain (STC). The results indicate the mosaic VLPs maintained the antigenic integrity of the variant and classic viruses and have the potential to serve as a multivalent vaccine for use in breeder flock.

Materials and Methods

Viruses

The IBDV variant strain USA08MD34p (GenBank Accession #GQ856676) was used to obtain pVP2 and VP3 sequences. The IBDV variant strain USA08MD34p was isolated from a Maryland broiler flock in 2008 (Jackwood 2010). The IBDV used to obtain the classic pVP2 sequences was Mo195 (GenBank Accession #AY780324). It was isolated from a Missouri broiler flock in 2004 (Jackwood 2005). The STC and V1 IBDV strains were used to challenge vaccinated specific-pathogen-free (SPF) chickens (Charles River Laboratories, North Franklin, Conn.). The V1 variant virus (GenBank Accession #AF281235) is pathogenic in SPF chickens and its amino acid sequence across the four P domains of VP2 is identical to Del-E (Jackwood 2001). The STC strain (GenBank Accession #D00499) is the classic standard challenge virus from the U.S. Animal and Plant Health Inspection Service (APHIS), National Veterinary Services Laboratory (Kibenge 1990).

Preparation of IBDV Gene Clones

The VP3 from IBDV strain USA08MD34p (variant strain) was amplified using a reverse transcriptase-polymerase chain reaction (RT-PCR) kit (SuperScript III One-step RT-PCR, Invitrogen, Life Technologies, Grand Island, N.Y.). The primers VP3F: 5'-GTACC TGATCACCATGGCTGCATCAGAGTTC-3' (SEQ ID NO: 1) and VP3R: 5'-CAGGA TGATCACTCAAGGTCCTCATCAGAG-3'(SEQ ID NO: 2) amplified the entire VP3 sequence from base 2,323 to base 3,123 of genome segment A. The start codon (ATG) in the forward primer is listed in italics and the underlined sequences are a genetic marker (not IBDV sequence) designed to identify the cloned gene.

The pVP2 portion of genome segment A was amplified from both the USA08MD34p and Mo195 viruses using a RT-PCR kit (SuperScript III One-step RT-PCR, Invitrogen) and the following primers: VP2F: 5'-TTCGA TGATCACGATGACAAACCTGTCAGATC-3' (SEQ ID NO: 3) and VP2R: 5'-ACTAC TGATCACCCCTTGTCGGCGGCGAGAG-3' (SEQ ID NO: 4). The start codon (ATG) in the forward primer is listed in italics and the underlined sequences are a genetic marker (not IBDV sequence) designed to identify the cloned gene. These primers amplify the entire pVP2 sequence from base 64 to base 1,635 of genome segment A.

For both the VP3 and pVP2 reactions the RT was at 55° C. for 45 min which was followed by 2 min denaturation at 95° C. The 40 PCR cycles consisted of 95° C. for 15 sec, 55° C. for 30 sec and 68° C. for 3.5 min. A 7 min hold at 68° C. was added to the end of the assay.

The 801 bp VP3 RT-PCR product and the 1,572 bp pVP2 RT-PCR products were ligated into the pGEM-T Easy vector (Promega Corp., Madison Wis.) using a Rapid Ligation Kit (Promega Corp.). Incubation for the ligation reaction was overnight at 4° C. The plasmids were then used to transform the E. coli strain HB-101 (Promega Corp.). The transformed bacteria were grown on L-agar containing 100 µg/ml ampicillin, 100 µg/ml X-gal and 0.1 µM IPTG at 37° C. overnight. White colonies were selected and grown overnight with shaking at 37° C. in 4.0 ml L-Broth containing 100 µg/ml ampicillin. The plasmids were extracted from 1.0 ml of the broth cultures using a Wizard Plus SV Minipreps DNA Purification System (Promega Corp.). Inserts were excised from the plasmids using EcoRI (Promega Corp.) and visualized on a 0.8% agarose gel.

Construction of Baculovirus Transfection Vectors

The pVL1393 baculovirus transfection vector (BD Biosciences, San Jose, Calif.) was used. The vector was linearized using EcoRI and then treated with 0.05 U Calf Intestinal Alkaline Phosphatase (Promega Corp.) at 37° C. for 1 hr. The reaction was stopped by adding 300 µl of a 20% SDS solution and the vector was phenol/chloroform extracted and ethanol precipitated with a 0.5 volume of 7.5M Ammonium Acetate (Sigma Chemical Co.).

The VP3 and pVP2 inserts that were excised from the pGEM-T Easy vectors were ligated into the linear pVL1393 vector using a Rapid Ligation Kit (Promega Corp.). Incubation was for 12 hours at 4° C. and the plasmids were then used to transform the E. coli strain HB-101 (Promega Corp.). The bacteria were placed onto L-agar containing 100 µg/ml ampicillin and incubated at 37° C. overnight. Bacterial colonies that grew on the agar plates were selected and grown in 4.0 ml L-Broth containing 100 µg/ml ampicillin at 37° C. with shaking overnight. The plasmids were extracted from a 1.0 ml volume of the bacterial cultures using a Wizard Plus SV Minipreps DNA Purification System (Promega Corp.).

To determine the orientation of the VP3 and pVP2 inserts in the pVL1393 plasmid, the constructs were cut with the restriction enzyme PstI and the fragments were visualized on a 0.8% agarose gel.

Transfection of Sf9 Insect Cells

The pVL1393 constructs containing VP3s and pVP2s in the correct orientation were used to transfect Sf9 insect cells. The BD BaculoGold Transfection Kit (BD Biosciences) was used. Briefly, the cell culture medium was removed from Sf9 cells growing in 6-well culture plates (Becton Dickinson Labware, Franklin Lakes, N.J.) and 1.0 ml of Transfection Buffer A was added to each of the 6 wells. Approximately 2.0 µg of each pVL1393 construct was added to 0.5 µg of the linearized Baculovirus DNA supplied in the BaculoGold kit. After a 5 min incubation at room temperature, 1.0 ml of Transfection Buffer B was added and the solution was gently agitated. This DNA mixture was then added slowly to the Sf9 cells and incubated at 27° C. for 4 hrs. Following this incubation, the transfection solution was removed from the cells and 3.0 ml of TNM-FH medium (BD-Biosciences) was gently added. Incubation continued at 27° C. for 4 days. The supernatants were then removed and half was stored at −70° C. until they could be examined for VP3 and pVP2 expression products while the other half was stored at 4° C. until they were used to inoculate new Sf9 cell cultures.

Detection of VP3 and pVP2 Nucleotide Sequences in Recombinant Baculoviruses

To determine if the transfections were successful, media from the transfected Sf9 cells were examined using PCR for the presence of VP3 and pVP2 nucleotide sequences in the recombinant Baculoviruses. The primers used for the VP3 sequences were the same as those used for cloning. For detection of the pVP2 sequences, a 743-bp segment of the hypervariable region of VP2 (hvVP2) from nucleotides 737 to 1479 was amplified using primers 743-1 (5'-GCCCA-GAGTCTACACCAT-3') (SEQ ID NO: 5) and 743-2 (5'-CCCGGATTATGTCTTTGA-3') (SEQ ID NO: 6) (Jackwood 2005).

Detection of pVP2 and Virus-Like Particle (VLP) Expression Products

The pVP2 protein was generated by infecting Sf9 cells with either the USA08MD34p-pVP2 baculovirus construct or the Mo195-pVP2 construct. The VLPs were prepared by inoculating Sf9 cells with the pVP2 constructs plus the USA08MD34p-VP3 baculovirus construct. Expression of the pVP2 proteins and VLPs was examined using an antigen-capture (AC)-ELISA (Synbiotics Corp., Kansas City, Mo.). The AC-ELISA plate contained the IBD screening monoclonal antibodies B69, R63 and #10. These monoclonal antibodies were reported to bind classic and variant VP2 proteins (Vakharia 1994). Supernatants from recombinant Baculovirus infected Sf9 cells were tested undiluted and at the following dilutions: 1:2, 1:4, 1:8, 1:16 and 1:64.

Visualization of VLPs

Transmission electron microscopy was used to determine the structural integrity of the VLPs expressed from Sf9 cells infected with the USA08MD34p-pVP2/USA08MD34p-VP3, Mo195-pVP2/USA08MD34p-VP3 and mosaic USA08MD34p-pVP2/Mo195-pVP2/USA08MD34p-VP3 combinations. Supernatants from the cell cultures were harvested 4 days post-inoculation. They were frozen and thawed once, clarified using slow speed centrifugation and then layered over 1.0 ml of a 20% sucrose solution in a 14×89 mm ultracentrifuge tube (Beckman, Palo Alto, Calif.). The samples were pelleted though the sucrose cushion in an ultracentrifuge at 150,000×g for 3 hrs. The pellets were rinsed with sterile $H_2O$ and then suspended in a 1.0 ml volume of sterile $H_2O$ before being stored at −70° C. A 250 volume of each VLP was place in an eppendorf tube and particulates were pelleted at 16,000×g for 2 min. The supernatants were then placed on formvar coated grids and stained with uranyl acetate for 2 min in the dark. Samples were examined using a transmission electron microscope (Hitachi H-7500) for VLPs.

Vaccination of Chickens with VLPs and Challenge

The VLPs were used to vaccinate 3 week old SPF chickens. The birds were bled prior to being vaccinated and were negative for IBDV antibodies. They were vaccinated with a 0.1 ml dose of the Sf9 cell cultures containing the USA08MD34p, Mo195 or mosaic VLPs. Inoculations were via the intramuscular route. Two weeks later, they were vaccinated with a second 0.1 ml dose of the same VLP samples via the subcutaneous route. The birds were then bled two weeks following the booster vaccination and the sera were examined for IBDV specific antibodies using an IBDxr ELISA kit (IDEXX, Corp.). The sera were also examined for virus-neutralizing (VN) antibody titers using a standard protocol and classic (S706) and variant (Del-E) antigens (Dybing 1998).

Two weeks following the booster vaccination, twenty birds that were vaccinated using the mosaic VLPs were allotted into 2 groups of ten birds each. One group was challenged with $10^2$ chick infectious doses $(CID)_{50}$ of the STC virus and the other with the same dose of the variant V1 strain of IBDV. Two groups of 6 SPF birds each that had not been vaccinated were also challenged with either the STC or V1 strains. A fifth group of 5 SPF birds served as non-vaccinated and non-challenged controls. At seven days following challenge all birds in the five groups were euthanized and examined for gross lesions in the bursa. The bursa and body weights of each bird were recorded.

Statistics

The bursa and body weights recorded at necropsy were used to calculate a bursa/body weight ratio (B/BW). Bursa/body weight (B/BW) ratios were calculated as the bursa weight (g)/body weight (g)×1000. These B/BW ratios were compared for statistical differences among the groups using the SAS: Proc GLM program.

Results

Cloning the pVP2 and VP3 Sequences

The RT-PCR products USA08MD34p-pVP2, Mo195-pVP2 and USA08MD34p-VP3 were ligated into the pGEM-T Easy vector and used to transform E. coli HB101 cells. White colonies were selected from the agar plates and examined for plasmids and IBDV sequences. The restriction enzyme EcoRI was used because it excises the IBDV sequences from the plasmid. The presence of 1,572 bp pVP2 inserts and 801 bp VP3 inserts were observed using agar gel electorphoresis (FIG. 1).

Insertion of the pVP2 and VP3 Clones into the Baculovirus Transfer Vector

Figure 2:
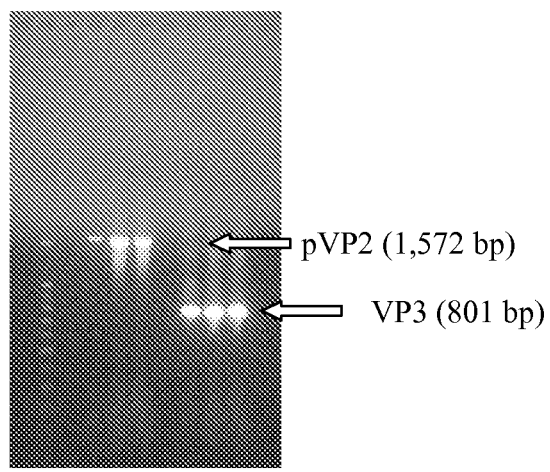
FIG. 2 shows purified pVP2 and VP3 inserts from the pGEM-T Easy vector.
Figure 3:
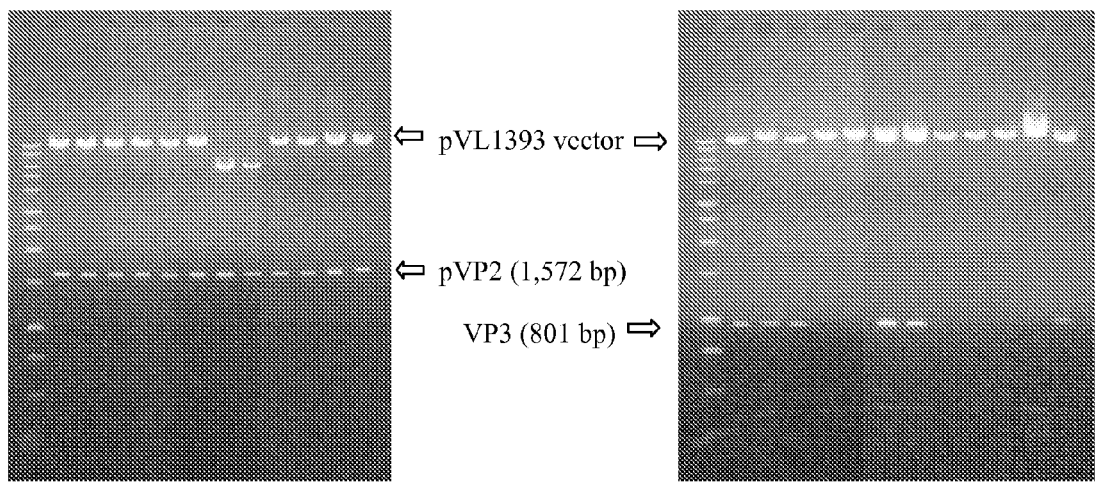
FIG. 3(A) shows pVP2 clones excised from pVL1393 using EcoRI. (B) VP3 clones excised from pVL1393 using EcoRI.

The pVL1393 Baculovirus transfer vector was used to insert the pVP2 and VP3 clones into the Baculovirus genome. The pVP2 and VP3 inserts from the pGEM-T Easy vectors were excised using EcoRI and purified on an agarose gel (FIG. 2). The inserts were then ligated into the pVL1393 plasmid that was cut with EcoRI and dephosphorlated. The resulting plasmids were used to transform E. coli HB-101 cells and then examined for IBDV sequences using the EcoRI enzyme and agarose gel electrophoresis (FIG. 3).

To express the pVP2 and VP3 sequences they must be downstream from the Baculovirus polyhedron promoter and in the correct direction. Because the pVL1393 vector was cut with one restriction enzyme, the pVP2 and VP3 clones could have been ligated into this vector in either direction. The orientation of the pVP2 inserts in the pVL1393 vector was determined using the enzyme PstI. This enzyme was selected because it cuts once in the plasmid and has multiple cut sites in the inserts. The pVP2 clones in the correct direction produce bands at 1,011 bp, 332 bp and 74 bp after digestion with PstI. Similarly the VP3 clones were cut with B gill to determine if they were in the correct orientation. This enzyme produces a band at 155 bp if the VP3 insert was ligated into the plasmid in the correct direction. The pVL1393 pVP2 and VP3 constructs in the correct direction were selected for Transfection into the Baculovirus genome. These constructs were also RT-PCR amplified and sequenced to insure they were in the correct orientation and contained uninterrupted open reading frames.

Transfection and Propagation of Recombinant Baculoviruses

The Sf9 cells and cell culture media were harvested 4 days following transfection of the pVP2 and VP3 sequences into the baculovirus genome. The samples were stored at 4° C. and then used to inoculate new cultures of Sf9 cells. Cytopathic effects (CPE) that consisted of floating cells and holes in the monolayer were observed at 3 and 4 days post-inoculation. Samples for protein expression were collected at 4 days post-inoculation and frozen at −70° C. Samples for further propagation of the recombinant Baculoviruses were collected at 4 days post-inoculation and stored at 4° C.

Using RT-PCR the pVP2 and VP3 nucleotide sequences were detected in the infected Sf9 cell cultures. To determine if the pVP2 proteins were being expressed the samples were tested in the AC-ELISA. The monoclonal antibodies on the AC-ELISA plate (Synbiotics) were reported to bind classic and variant viruses. The optical density readings for the samples tested are shown in Table 1. The amino acids and nucleic sequence of the proteins and nucleotides sent forth in Table 1 are in SEQ ID NOS. 7-12:

TABLE 1

| Description | SEQ ID NOs |
|---|---|
| Variant Virus pp34 VP3 Nucleotide Sequence | SEQ ID NO: 7 |
| Variant Virus pp34 VP3 Amino Acid Sequence | SEQ ID NO: 8 |
| Variant Virus pp34 pVP2 Nucleotide Sequence | SEQ ID NO: 9 |
| Variant Virus pp34 pVP2 Amino Acid Sequence | SEQ ID NO: 10 |
| Classic Virus Mo195 pVP2 Nucleotide Sequence | SEQ ID NO: 11 |
| Classic Virus Mo195 pVP2 Amino Acid Sequence | SEQ ID NO: 12 |

The results indicate the Mo195-pVP2 construct was expressing this protein. The USA08MD34p-pVP2 and USA08MD34p-VP3 constructs were negative in the AC-ELISA. The negative USA08MD34p-VP3 result was expected since monoclonal antibodies B69, R63 and #10 do not bind this protein.

Because the AC-ELISA results for the first USA08MD34p-pVP2 Baculovirus construct were negative, a second Baculovirus construct was prepared from a different clone and tested in the RT-PCR assay. This new USA08MD34p-pVP2 Baculovirus was positive in the RT-PCR assay. However, when it was tested for expression of pVP2 using the AC-ELISA the results were also negative. Since it is possible the AC-ELISA monoclonal antibodies do not bind the USA08MD34p-pVP2 protein, this second construct was used in subsequent experiments to produce virus-like particles (VLPs).

Production of Virus-Like Particles (VLPs)

The production of VLPs was initiated by inoculating monolayers of Sf9 cells with the USA08MD34p-VP3 Baculovirus. These cell cultures were then inoculated with either the USA08MD34p-pVP2 or Mo195-pVP2 Baculoviruses. After 4 days of incubation at 27° C. the cultures were observed to have CPE and they were frozen at −70° C. The USA08MD34p-pVP2/VP3 and Mo195-pVP2/VP3 cultures were tested in the AC-ELISA for protein expression (Table 2). The optical density readings for the Mo195 VLPs were strongly positive. The USA08MD34p VLPs were also positive in the AC-ELISA, showing the monoclonal antibodies do not bind the USA08MD34p-pVP2 but they do bind the USA08MD34p proteins when the pVP2 is combined with VP3 into a VLP.

The Mo195 and USA08MD34p VLPs were examined using electron microscopy for the presence of particles that resembled IBDV. Both cultures contained numerous IBDV like particles (VLPs) (FIG. 4) and the un-inoculated control Sf9 cultures were negative for VLPs. The VLPs varied in size from 40 nm to 80 nm but most were approximately 60 nm.

TABLE 2

AC-ELISA and assays for antibody titers to VLPs.

| Construct | AC-ELISA Optical Density[1] | ELISA Antibody titers[2] | VN Antibody titers[3] | |
|---|---|---|---|---|
| | | | Variant | Classic |
| USA08MD34p-pVP2 | 0.231 | NA | NA | NA |
| Mo195-pVP2 | 0.640 | NA | NA | NA |
| USA08MD34p-VP3 | 0.116 | NA | NA | NA |
| Sf9 Negative Control[4] | 0.241 | NA | NA | NA |
| USA08MD34p-VLP | 0.797 | 2,042 | 150 | <50 |
| Mo195-VLP | 1.379 | 9,130 | <50 | 1,200 |
| Mosaic VLP[5] | ND | 1,254 | 229 | 185 |
| Sf9 Negative Control | 0.375 | 0 | <50 | <50 |

[1]AC-ELISA optical density >0.600 = positive, 0.300-0.600 = suspect positive, <0.300 = negative (Synbiotics, Corp. Technical Insert). ND = Not determined.
[2]The IDEXX IBD-XR assay was used. NA = Not applicable. Antisera were only prepared in chickens to the VLP constructs.
[3]The VN titers were only determined for VLP samples. The cell culture adapted viruses used were Del-E for the variant antigen and S706 for the classic antigen.
[4]The negative controls consisted of non-inoculated Sf9 cell cultures.
[5]The mosaic VLPs contained VP2 from both the USA08MD34p and Mo195 strains.

Figure 4:
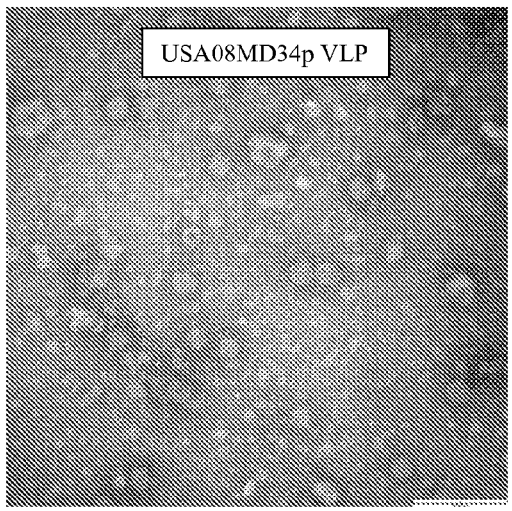
FIG. 4 shows virus-like particles (VLPs) prepared in Sf9 cell cultures infected with recombinant Baculoviruses. The pVP2 from the variant USA08MD34p or classic Mo195 IBDV strains were co-expressed with USA08MD34p-VP3. The mosaic VLPs contained pVP2 from the variant and classic viruses. The horizontal bar on the bottom right of each electron micrograph represents 200 nm.
Figure 4:
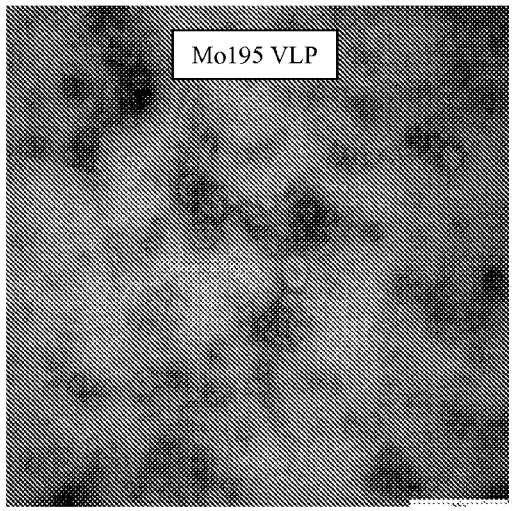
Figure 4:
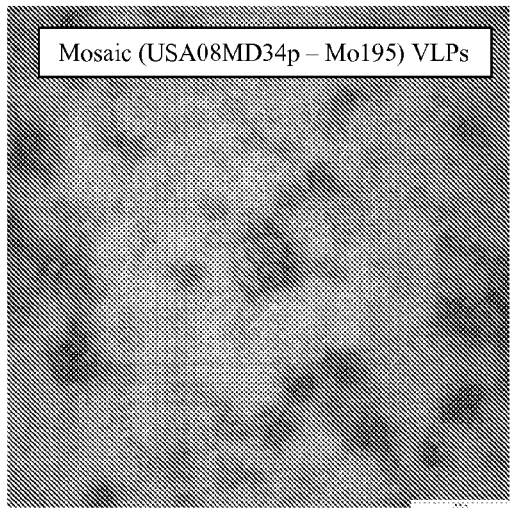
Figure 4:
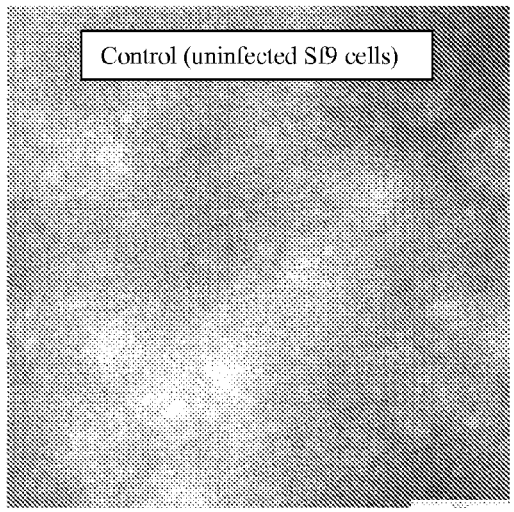

The Mo195-VP2, USA08MD34p-VP2 and USA08MD34p-VP3 were inoculated into Sf9 cells to produce VLPs containing both classic and variant pVP2 antigens. The resulting mosaic VLPs resembled the capsid structure of IBDV (FIG. 4).

Serology and Challenge Experiment

The Mo195, USA08MD34p and mosaic VLPs were used to vaccinate SPF chickens. The three-week-old SPF birds were negative for IBDV antibodies prior to being vaccinated. Two weeks following booster vaccination using either USA08MD34p, Mo195 or mosaic VLPs, the sera from vaccinated birds were positive in the ELISA and VN assays. The ELISA antibody titers to IBDV and the virus-neutralization (VN) antibody titers are reported in Table 2. The USA08MD34p and Mo195 VLPs were immunogenic in chickens and produced IBDV specific antibodies detected in the ELISA. The VN data indicate the antibodies produced were capable of neutralizing IBDV strains in cell culture. The Mo195-VLP antisera neutralized 5706 (mean titer=1, 200). When these sera were tested using the Del-E antigen the neutralizing titer was negative. The USA08MD34p-VLP antisera neutralized the Del-E antigen but the titer was low (mean titer=150). When these sera were tested against the 5706 antigen, no neutralizing antibodies were detected. The mosaic VLPs containing VP2 from both USA08MD34p and Mo195 produced ELISA titers and neutralizing antibodies to both the classic (S706) and variant (Del-E) IBDV strains (Table 2).

The mean VN titers to both variant and classic antigens were relatively low compared to the mean ELISA titer for these mosaic VLPs however, challenge of these birds with the classic STC or variant V1 strains indicated they were protected (Table 3). The STC challenge virus produced gross lesions in the bursas of all 6 birds in the non-vaccinated STC control group. This was not evident in the B/BW ratios of this group since STC typically causes an enlarged edematous bursa prior to atrophy. The six V1 challenged birds in the V1 control group all had small friable bursas typical of this variant virus. Their mean B/BW ratios were significantly different ($p<0.05$) compared to the non-vaccinated and non-challenged controls. No gross lesions were observed in the bursas of mosaic VLP vaccinated birds challenged with STC. One of the ten birds in the mosaic VLP vaccinated group that was challenged with V1 had a small bursa typical of a variant virus infection. The bursas of the other nine birds in this group appeared normal. The mean B/BW ratios of birds in the mosaic VLP vaccinated and challenged groups were not statistically different from the non-vaccinated, non-challenged controls (Table 3).

TABLE 3

Necropsy results of mosaic VLP vaccinated birds following challenge.

| Group | Challenge Virus[1] | Lesions[2] | Bursa/Body wt Ratios[3] |
|---|---|---|---|
| Control | None | 0/5 | $4.71 \pm 0.71^a$ |
| STC Control | STC | 6/6 | $4.40 \pm 0.77^a$ |
| V1 Control | V1 | 6/6 | $1.86 \pm 0.37^b$ |
| Mosaic VLP[4] | STC | 0/10 | $4.54 \pm 0.95^a$ |
| Mosaic VLP | V1 | 1/10 | $3.67 \pm 1.22^a$ |

[1]The challenge viruses were given at $10^{2.0}$ $CID_{50}$/bird. The birds were challenged 7 days following the last booster vaccination.
[2]Number of birds with gross lesions in the bursa/total number of birds in the group.
[3]Bursa/body weight ratios ± standard deviation.
[4]The mosaic VLPs contained VP2 from both the USA08MD34p and Mo195 strains.

Discussion

As described herein, the Baculovirus expression system was used to create an alternative to bursa derived IBDV antigens that can be used in breeder flock vaccines.

The molecular expression of IBDV proteins that are immunogenic has been reported but these subunit proteins have not been successfully integrated into an efficacious vaccine for IBD (Dybing 1998; Vakharia 1997; Vakharia 1994; Pitcovski 1996; Martinez 2000). As shown herein, pVP2s from a variant and a classic IBDV were co-expressed with VP3 in a Baculovirus system to produce VLPs. This differs from previous studies in that the Baculovirus expressed pVP2 from the variant and classic viruses were incorporated into a mosaic VLP product containing both antigenic types of the viral protein.

The USA08MD34p and Mo195 represent variant and classic viruses respectively. The pVP2 expression products from the Mo195 virus tested positive in the AC-ELISA but the pVP2 from USA08MD34p was negative in this assay. This result was surprising since the co-expression of USA08MD34p-VP2 With USA08MD34p-VP3 produced VLPs that were detected in the AC-ELISA and by electron microscopy. Furthermore, inoculation of the USA08MD34p VLPs in chicks produced anti-IBDV antibodies. The AC-ELISA screening plate (Synbiotics, Corp) contains the monoclonal antibodies R63, B69 and #10. The reactivity of these monoclonal antibodies with classic and variant IBDV strains indicates they should be useful in detecting both antigenic types of the virus (Vakharia 1994). All three monoclonal antibodies map to the P domain of VP2 but individually, R63, B69 and #10 do not detect all IBDV strains (Vakharia 1994; Letzel 2007). Substitution mutations in the USA08MD34p virus may have altered the epitopes such that these monoclonal antibodies were unable to bind the Baculovirus expressed USA08MD34p-VP2. Detection of the USA08MD34p VLP in the AC-ELISA indicates one or more of the monoclonal antibodies bind a tertiary epitope formed by the pVP2 trimer or an epitope was hidden when the VP2 was singularly expressed but exposed when it was co-expressed with VP3. The result shows that VLP capsid structures are higher quality antigens than VP2 tubules and polyprotein derived mixed structures (Martinez 2003).

Specific antibodies to IBDV were detected by the ELISA in serum samples from chickens vaccinated with all the VLP constructs. The ELISA cannot distinguish between antibodies to variant and classic viruses. Using a Del-E variant virus and an 5706 classic virus adapted to replicate in cell culture, the serum samples were examined in vitro for variant and classic specific neutralizing antibodies.

When the mosaic VLPs contained pVP2 from both USA08MD34p and Mo195, neutralizing antibodies to both the Del-E and 5706 antigens were observed. The result indicates both classic and variant pVP2 expression products were incorporated into the VLP vaccine. Not only was the antigenic integrity maintained but the immunity induced by the mosaic VLPs protected chickens against pathogenic classic (STC) and variant (V1) IBDV strains. Furthermore, these mosaic VLPs have the ability to induce maternal immunity that protects progeny chicks from pathogenic variant and classic viruses.

Example 2

The Use of ELISA as a Diagnostic

Antigen for coating ELISA plates was prepared by infecting SF9 insect cells with a combination of recombinant Baculoviruses expressing pVP2 and VP3. The infected cells produced VLPs and were harvested 4 days following infection. The VLPs were diluted 1:5 in PBS (1.9 mM NaH2P04, 8.1 mM Na2HP04, 154 mM NaCl (pH7.2]) containing 0.05% (wt/vol) sodium azide and used to coat 96-well flat-bottom plates (Falcon; Becton Dickinson, Lincoln Park, N.J.). This dilution of antigen was determined to be optimal using standard procedures. A 50 ul volume of the diluted VLP antigen was used to coat each well of a 96-well plate for 24 hrs at room temperature. The antigen-coated 96-well plates were washed three times in water and then incubated at room temperature for 30 min in blocking buffer (170 mM"H3B04 [pH 8.5], 120 mM NaCl, 1 mM EDTA, 0.05% [wt/vol] sodium azide, 0.25% [wt/vol] bovine serum albumin, 0.05% [vol/vol] Tween 20). After three washes in water, a 50 ul volume of serum diluted in blocking buffer was added to each well. Incubation continued at room temperature for 30 min. The ELISA plates were then washed three times in water, once for 10 min in blocking buffer, and then three times in water. A horseradish peroxidase-labeled goat anti-chicken immunoglobulin G was used according to the manufacturer's directions. A 50 ul volume was added to each well. Plates were incubated at room temperature for 30 min and then washed in water, in blocking buffer, and again in water as described above. A 75 ul volume of the substrate was added, and after 15 min the color development was stopped with 5% (wt/vol) SDS in water. Test wells were read on an ELISA reader at a wavelength of 620 nm.

The VLP antigens reacted with the serum antibodies to IBDV and produced a positive result in the ELISA. Chicken serum samples from birds not exposed to IBDV were negative in the assay. The results indicate that VLP antigens can be used in the ELISA to detect antibodies to IBDV strains.

Example 3

Breeder Vaccination and Progeny Challenge Study for Very Virulent Strain

The VLP vaccine for vvIBDV can be used to produce maternal immunity in chickens. The VLP vvIBDV vaccine can be added to an existing commercial product designed for breeder bird vaccination or can be used alone. To test the efficacy of such a vaccine, breeder birds are vaccinated and their progeny are tested for immunity to a vvIBDV challenge strain.

1. Vaccines: Commercial Killed Breeder vaccine
    Commercial Killed Breeder vaccine with vvIBDV-VLP
2. Experimental Design:
    1. Divide the Broiler Breeders into two groups. One group is vaccinated with the Commercial Killed Breeder vaccine and another is given the same vaccine with the vvIBDV-VLP added. A third group receives only the vvIBDV VLP vaccine and a fourth group contains non-vaccinated control breeder birds.
    2. Collect fertile eggs and hatch chicks
    3. Test chicks for antibodies to IBDV using the ELISA or virus-neutralization assays.
    4. Challenge chicks at 1, 2 and 3 weeks of age with vvIBDV to assess the maternal immunity to this virus.
    5. Necropsy chicks one-week following challenge and determine the gross and histopathologic lesions. Test the bursa tissues for the presence of vvIBDV using molecular techniques.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

[1] Dobos P, Hill B, Hallett R, Kells D, Becht H, Teninges D. Biophysical and Biochemical Characterization of Five Animal Viruses with Bisegmented Double-Stranded RNA Genomes. J Virol 1979; 32:593-605.

[2] von Einem U I, Gorbalenya A E, Schirrmeier H, Behrens S E, Letzel T, Mundt E. VP1 of infectious bursal disease virus is an RNA-dependent RNA polymerase. J Gen Virol 2004; 85:2221-9.

[3] Birghan C, Mundt E, Gorbalenya A E. A non-canonical Lon proteinase lacking the ATPase domain employs the Ser-Lys catalytic dyad to exercise broad control over the life cycle of a double-stranded RNA virus. EMBO Journal 2000; 19:114-23.

[4] Kibenge F S B, Dhillon A S, Russell R G. Biochemistry and Immunology of Infectious Bursal Disease Virus. J Gen Virol 1988; 69:1757-75.

[5] Galloux M, Libersou S, Morellet N, et al. Infectious Bursal Disease Virus, a Non-enveloped Virus, Possesses a Capsid-associated Peptide that Deforms and Perforates Biological Membranes. J Biological Chemistry 2007; 282:20774-84.

[6] Coulibaly F, Chevalier C, Delmas B, Rey F A. Crystal structure of an aquabirnavirus particle: Insights into antigenic diversity and virulence determinism. J Virol 2010; 84:1792-9.

[7] Coulibaly F, Chevalier C, Gutsche I, et al. The Birnavirus crystal structure reveals structural relationships among icosahedral viruses. Cell 2005; 120:761-72.

[8] Caston J R, Martinez-Torrecuadrada J L, Maraver A, Lombardo E, Rodriguez J F. C terminus of infectious bursal disease virus major capsid protein VP2 is involved in definition of the T number for capsid assembly. J Virol 2001; 75(22):10815-28.

[9] Maraver A, Clemente R, Rodriguez J F, Lombardo E. Identification and Molecular Characterization of the RNA Polymerase-Binding Motif of Infectious Bursal Disease Virus Inner Capsid Protein VP3. J Virol 2003; 77, No. 4:2459-68.

[10] Lombardo E, Maraver A, Caston J R, et al. VP1, the putative RNA-dependent RNA polymerase of infectious bursal disease virus, forms complexes with the capsid protein VP3, leading to efficient encapsidation into virus-like particles. J Virol 1999; 73:6973-83.

[11] Martinez-Torrecuadrada J L, Caston J R, Castro M, Carrascosa J L, Rodriguez J F, Casal J I. Different Architectures in the Assembly of Infectious Bursal Disease Virus Capsid Proteins Expressed in Insect Cells. Virology 2000; 278:322-31.

[12] Ona A, Luque D, Abaitua F, Maraver A, Caston J R, Rodriguez J F. The C-terminal domain of the pVP2 precursor is essential for the interaction between VP2 and VP3, the capsid polypeptides of infectious bursal disease virus. Virology 2004; 322:135-42.

[13] Heine H G, Haritou M, Failla P, Fahey K, Azad A A. Sequence analysis and expression of the host-protective immunogen VP2 of a variant strain of infectious bursal disease virus which can circumvent vaccination with standard type I strains. J Gen Virol 1991; 72:1835-43.

[14] Eterradossi N, Toquin D, Rivallan G, Guittet M. Modified activity of a VP2-located neutralizing epitope on various vaccine, pathogenic and hypervirulent strains of infectious bursal disease virus. Arch Virol 1997; 142:255-70.

[15] Eterradossi N, Arnauld C, Toquin D, Rivallan G. Critical amino acid changes in VP2 variable domain are associated with typical and atypical antigenicity in very virulent infectious bursal disease viruses. Arch Virol 1998; 143:1627-36.

[16] Vakharia V N, He J, Ahamed B, Snyder D B. Molecular basis of antigenic variation in infectious bursal disease virus. Virus Res 1994; 31:265-73.

[17] Letzel T, Coulibaly F, Rey F A, et al. Molecular and structural bases for the antigenicity of VP2 of infectious bursal disease virus. J Virol 2007; 81:12827-35.

[18] Schnitzler D, Bernstein F, Muller H, Becht H. The genetic basis for the antigenicity of the VP2 protein of the infectious bursal disease virus. J Gen Virol 1993; 74:1563-71.

[19] Jackwood D J, Sommer-Wagner S E. Amino acids contributing to antigenic drift in the infectious bursal disease Birnavirus (IBDV). Virology 2011; 409:33-7.

[20] Jackwood D J, Sommer-Wagner S E. Detection and characterization of infectious bursal disease viruses in broilers at processing. Preventive Veterinary Medicine 2010; 97:45-50.

[21] Jackwood D J, Sommer-Wagner S E. Molecular epidemiology of infectious bursal disease viruses: Distribution and genetic analysis of newly emerging viruses in the United States. Avian Dis 2005; 49:220-6.

[22] Jackwood D J, Sommer S E, Knoblich H V. Amino Acid Comparison of Infectious Bursal Disease Viruses Placed in the Same or Different Molecular Groups by RT/PCR-RFLP. Avian Dis 2001; 45:330-9.

[23] Kibenge F S B, Jackwood D J, Mercado C C. Nucleotide sequence analysis of genome segment A of infectious bursal disease virus. J Gen Virol 1990; 71:569-77.

[24] Jackwood D J, Sommer-Wagner S E. Molecular studies on suspect very virulent infectious bursal disease virus genomic RNA samples. Avian Dis 2005; 49:246-51.

[25] Dybing J K, Jackwood D J. Antigenic and immunogenic properties of baculovirus-expressed infectious bursal disease viral proteins. Avian Dis 1998; 42:80-91.

[26] van den Berg T P, Eterradossi N, Toquin D, Meulemans G. Infectious bursal disease (Gumboro Disease). World Trade and Public Health Implications, OIE Scientific and Technical Rev 2000; 19:509-43.

[27] Vakharia V N, Snyder D B, Lutticken D H, Mengel-Whereat S A, Edwards G H, Goodwin M A. Active and passive protection against variant and classic infectious bursal disease virus strains induced by baculovirus-expressed structural proteins. Vaccine 1994; 12:452-6.

[28] Vakharia V N, Snyder D B, He J, Edwards G H, Savage P K, Mengel-Whereat S A. Infectious bursal disease virus structural proteins expressed in a baculovirus recombinant confer protection in chickens. J Gen Virol 1993; 74:1201-6.

[29] Pitcovski J, Di-Castro D, Shaaltiel Y, et al. Insect cell-derived VP2 of infectious bursal disease virus confers protection against the disease in chickens. Avian Dis 1996; 40:753-61.

[30] Martinez-Torrecuadrada J L, Lazaro B, Rodriguez J F, Casal J I. Antigenic Properties and Diagnostic Potential of Baculovirus-Expressed Infectious Bursal Disease Virus Proteins VPX and VP3. Clin and Diag Lab Immunol 2000 Jul. 1; 7:645-51.

[31] Martinez-Torrecuadrada J L, Saubi N, Pages-Mante' A, Caston J R, Espuna E, Casal J I. Structure-dependent efficacy of infectious bursal disease virus (IBDV) recombinant vaccines. Vaccine 2003; 21:1952-60.

[32] Coulibaly F, Chevalier C, Delmas B, Rey F A. Crystal Structure of an Aquabirnavirus Particle: Insights into Antigenic Diversity and Virulence Determinism. J Virol 2009; 84:1792-9.

SEQUENCES

SEQ ID NO: 1
GTACCTGATCACCATGGCTGCATCAGAGTTC

SEQ ID NO: 2
CAGGATGATCACTCAAGGTCCTCATCAGAG

SEQ ID NO: 3
TTCGATGATCACGATGACAAACCTGTCAGATC

SEQ ID NO: 4
ACTACTGATCACCCCTTGTCGGCGGCGAGAG

SEQ ID NO: 5
GCCCAGAGTCTACACCAT

SEQ ID NO: 6
CCCGGATTATGTCTTTGA

Variant Virus pp34 VP3 Nucleotide Sequence
SEQ ID NO: 7
GTACCTGATCACCATGGCTGCATCAGAGTTCAAAGAGACCCCTGAACTCGAGAGCGCCGTCAGAGCCATGGAG
GCAGCAGCCAATGTGGACCCACTGTTCCAATCTGCACTCAGTGTGTTCATGTGGCTGGAAGAGAATGGGATTG
TGACTGACATGGCCAACTTCGCACTCAGCGACCCGAACGCCCATCGGATGCGAAATTTTCTTGCAAACGCACC
ACAAGCAGGCAGCAAGTCGCAAAGGGCCAAGTACGGGACAGCAGGCTACGGAGTGGAGGCCCGGGGCCCCACA
CCAGAGGAAGCACAGAGGGAAAAAGACACACGGATCTCAAAGAAGATGGAGACCATGGGCATCTACTTTGCGA
CACCGGAATGGGTAGCACTCAATGGGCACCGAGGGCCAAGCCCAGGCCAGCTAAAGTACTGGCAGAACACACG
AGAAATACCGGACCCAAATGAGGACTATCTAGACTACGTGCATGCAGAGAAGAGCCGGTTGGCATCAGAAGAA
CAAATCCTAAGGGCAGCTACGTCGATCTACGGGGCTCCAGGACAGGCAGAGCCACCCCAAGCTTTCATAGATG
AAGTTGCCAAAGTCTATGAAATCAACCATGGACGTGGCCCCAACCAAGAACAGATGAAAGATCTGCTCTTGAC
TGCCATGGAGATGAAGCATCGCAATCCCAGGCGGGCTCCACCAAAGCCCAAGCCAAAACCCAATGCTCCAACA
CAGAGACCCCCTGGTCGGCTGGGCCGCTGGATCAGGACTGTCTCTGATGAGGACCTTGAGTGATCATCCTG Variant Virus pp34 VP3 Amino Acid Sequence
SEQ ID NO: 8
MAASEFKETPELESAVRAMEAAANVDPLFQSALSVFMWLEENGIVTDMANFALSDPNAHRMRNFLANAPQAGS
KSQRAKYGTAGYGVEARGPTPEEAQREKDTRISKKMETMGIYFATPEWVALNGHRGPSPGQLKYWQNTREIPD
PNEDYLDYVHAEKSRLASEEQILRAATSIYGAPGQAEPPQAFIDEVAKVYEINHGRGPNQEQMKDLLLTAMEM
KHRNPRRAPPKPKPKPNAPTQRPPGRLGRWIRTVSDEDLE*

Variant Virus pp34 pVP2 Nucleotide Sequence
SEQ ID NO: 9
AACGATGATCACGATGACAAACCTGTCAGATCAAACCCAACAGATTGTTCCGTTCATACGGAGCCTTCTGATG
CCAACAACCGGACCGGCGTCCATTCCGGACGACACCCTGGAGAAGCACACTCTCAGGTCAGAGACCTCGACCT
ACAATTTGACTGTGGGGACACAGGGTCAGGGCTAATTGTCTTTTTCCCTGGCTTCCCTGGCTCAATTGTGGG
TGCTCACTACACACTGCAGAGCAATGGGAACTACAAGTTCAATCAGATGCTCCTGACGGCACAGAACCTACCG
GCCAGCTACAACTACTGCAGGCTAGTGAGTCGGAGTCTCACAGTAAGGTCAAGCACACTCCCTGGTGGCGTTT
ATGCACTAAACGGCACCATAAACGCCGTGACCTTCCAAGGAAGCCTGAGTGAACTGACAGATGTTAGCTACAA
TGGGTTGATGTCTGCAACAGCCAACATCAACGACAAAATCGGGAACGTCCTAGTAGGGGAAGGGGTCACCGTC
CTCAGCTTACCCACATCATATGATCTTGGGTATGTGAGGCTTGGTGACCCCATACCCGCTATAGGGCTTGACC
CAAAAATGGTAGCAACATGTGACAGCAGTGACAGGCCCAGAGTCTACACCATAACTGCAGCCGATAATTACCA
ATTCTCATCACAGTACCAAACAGGTGGGGTAACAATCACACTGTTCTCGGCCAACATTGATGCTATCACAAGT
CTCAGCGTTGGGGGGAGCTCGTGTTCAAAACAAGTGTCCAAAACCTTGTACTGGGCGCCACCATCTACCTTA
TAGGCTTTGATGGGACTGCGGTAATCACCAGAGCCGTGGCCGCAAACAATGGGCTGACGGCCGGTATCGACAA
TCTTATGCCATTCAATCTTGTGATTCCGACCAACGAGATAACCCAACCAATCACATCCATCAAACTGGAGATA
GTGACCTCCAAAAGTGATGGTCAGGCAGGGGAACAGATGTCATGGTCGGCAAGTGGGAGCCTAGCAGTGACGA -continued

```
TCCATGGTGGCAACCATCCAGGAGCCCTCCGTCCCGTCACACTAGTGGCCTACGAAAGAGTGGCAACAGGATC
TGTCGTTACGGTCGCTGGGGTGAGCAACTTCGAGCTGATCCCAAATCCTGAACTAGCAAAGAACCTGGTTACA
GAATACGGCCGATTTGACCCAGGAGCCATGAACTACACAAAATTAATACTGAGTGAGAGGGACCGCCTTGGCA
TCAAGACTGTCTGGCCAACAAGGGAGTACACTGACTTTCGTGAGTACTTCATGGAGGTGGCCGACCTCAACTC
TCCCCTGAAGATTGCAGGAGCATTTGGCTTCAAAGACATAATCCGGGCCATAAGGAGGATAGCTGTGCCGGTG
GTCTCTACACTGTTCCCACCTGCTGCTCCTCTGGCCCATGCAATTGGGGAAGGTGTAGACTACCTGCTGGGCG
ATGAGGCACAGGCTGCTTCAGGAACTGCTCGAGCCGCGTCAGGAAAAGCAAGGGCTGCCTCAGGCCGCATAAG
GCAGCTGACTCTCGCCGCCGACAAGGGGTGATCAGTATGT
```

Variant Virus pp34 pVP2 Amino Acid Sequence
SEQ ID NO: 10
```
MTNLSDQTQQIVPFIRSLLMPTTGPASIPDDTLEKHTLRSETSTYNLTVGDTSGLIVFFPGFPGSIVGAHYT
LQSNGNYKFNQMLLTAQNLPASYNYCRLVSRSLTVRSSTLPGGVYALNGTINAVTFQGSLSELTDVSYNGLMS
ATANINDKIGNVLVGEGVTVLSLPTSYDLGYVRLGDPIPAIGLDPKMVATCDSSDRPRVYTITAADNYQFSSQ
YQTGGVTITLFSANIDAITSLSVGGELVFKTSVQNLVLGATIYLIGFDGTAVITRAVAANNGLTAGIDNLMPF
NLVIPTNEITQPITSIKLEIVTSKSDGQAGEQMSWSASGSLAVTIHGGNHPGALRPVTLVAYERVATGSVVTV
AGVSNFELIPNPELAKNLVTEYGRFDPGAMNYTKLILSERDRLGIKTVWPTREYTDFREYFMEVADLNSPLKI
AGAFGFKDIIRAIRRIAVPVVSTLFPPAAPLAHAIGEGVDYLLGDEAQAASGTARAASGKARAASGRIRQLTL
AADKG*
```

Classic Virus Mo195 pVP2 Nucleotide Sequence
SEQ ID NO: 11
```
AACGATGATCACGATGACAAACCTGTCAGATCAAACCCAACAGATTGTTCCGTTCATACGGAGCCTTCTGATG
CCAACAACCGGACCGGCGTCCATTCCGGACGACACCCTGGAGAAGCACACTCTCAGGTCAGAGACCTCGACTT
ACAATTTGACTGTGGGGACACAGGGTCAGGGCTAATTGTCTTTTTCCCTGGATTCCCTGGCTCAATTGTGGG
TGCTCACTACACACTGCAGAGCAATGGGAACTACAAGTTCGATCTCCTGACTGCCCAGAACCTACCG
GCCAGCTACAACTACTGCAGGCTAGTGAGTCGGAGTCTCACAGTAAGGTCAAGCACACTCCCTGGTGGCGTTT
ATGCACTAAACGGCACCATAAACGCCGTGACCTTCCAAGGAAGCCTGAGTGAGCTGACAGATGTTAGCTACAA
TGGGTTGATGTCTGCAACAGCCAACATCAACGACAAAATTGGGAACGTCCTAGTAGGGGAAGGAGTCACCGTC
CTCAGCCTACCCCACATCATATGATCTTGGGTATGTGAGGCTTGGTGACCCCATACCCGCTATAGGGCTTGACC
CAAAAATGGTAGCAACATGTGACAGCAGTGACAGGCCCAGAGTCTACACCATAACCGCAGCTGATGATTACCA
ATTCTCATCACAGTACCAACCAGGTGGGGTAACAATCACACTGTTCTCAGCCAACATTGATGCCATCACAAGC
CTCAGCGTCGGGGAGAGCTCGTGTTCAAAACCAGCGTCCAAAGCCTTGTACTGGGCGCCACCATCTACCTCA
TAGGGTTTGATGGGACTGCGGTAATCACCAGAGCTGTGGCCGCAAACAATGGGCTGACGGCCGGCATCGACAA
TCTTATGCCATTCAATCTTGTGATTCCAACCAACGAGATAACCCAGCCAATCACATCCATCAAATTGGAGATA
GTTACCTCCAAAAGTAGTGGTCAGGAAGGGGATCAGATGTCATGGTCGGCAAGTGGGAGCCTAGCAGTGACGA
TCCATGGTGGCAACTATCCAGGGGCCCTCCGTCCCGTCACACTAGTAGCTTACGAAAGAGTGGCAACAGGATC
TGTCGTTACGGTCGCTGGGGTGAGCAACTTCGAGCTGATCCCCAAATCCTGAACTAGCAAAGAACCTGGTTACA
GAATACGGCCGATTTGACCCAGGAGCCATGAACTACACAAAATTGATACTGAGTGAGAGGGACCGTCTTGGCA
TCAAGACCGTCTGGCCAACAAGGGAGTACACTGACTTTCGTGAGTACTTCATGGAGGTGGCCGACCTCAACTC
TCCCCTGAAGATTGCAGGAGCATTTGGCTTCAAAGATATTATCCGGGCCATAAGGAGGATAGCTGTGCCGGTG
GTCTCTACATTGTTCCCACCTGCTGCTCCCCTAGCCCATGCAATTGGGGAAGGTGTAGACTACCTGCTGGGCG
ATGAGGCACAGGCTGCTTCAGGAACTGCTCGAGCCGCGTCAGGAAAAGCAAGGGCTGCCTCAGGCCGCATAAG
GCAGCTAACTCTCGCCGCCGACAAGGGGTGATCAGTATGT
```

Classic Virus Mo195 pVP2 Amino Acid Sequence
SEQ ID NO: 12
```
MTNLSDQTQQIVPFIRSLLMPTTGPASIPDDTLEKHTLRSETSTYNLTVGDTSGLIVFFPGFPGSIVGAHYT
LQSNGNYKFDQMLLTAQNLPASYNYCRLVSRSLTVRSSTLPGGVYALNGTINAVTFQGSLSELTDVSYNGLMS
ATANINDKIGNVLVGEGVTVLSLPTSYDLGYVRLGDPIPAIGLDPKMVATCDSSDRPRVYTITAADDYQFSSQ
YQPGGVTITLFSANIDAITSLSVGGELVFKTSVQSLVLGATIYLIGFDGTAVITRAVAANNGLTAGIDNLMPF
NLVIPTNEITQPITSIKLEIVTSKSSGQEGDQMSWSASGSLAVTIHGGNYPGALRPVTLVAYERVATGSVVTV
AGVSNFELIPNPELAKNLVTEYGRFDPGAMNYTKLILSERDRLGIKTVWPTREYTDFREYFMEVADLNSPLKI
AGAFGFKDIIRAIRRIAVPVVSTLFPPAAPLAHAIGEGVDYLLGDEAQAASGTARAASGKARAASGRIRQLTL
AADKG*
```

Classic IBDV (FD181) VP3 Nucleotide Sequence
SEQ ID NO: 13
```
GTACCTGATCACCATGGCTGCATCAGAGTTCAAAGAGACCCCCGAACTCGAGAGTGCCGTCAGAGCAATGGAA
GCAGCAGCCAACGTGGACCCACTATTCCAATCTGCACTCAGTGTGTTCATGTGGCTGGAAGAGAATGGGATTG
TGACTGACATGGCCAACTTCGCACTCAGCGACCCGAACGCCCATCGGATGCGAAATTTTCTTGCAAACGCACC
ACAAGCAGGCAGCAAGTCGCAAAGGGCCAAGTACGGGACAGCAGGCTACGGAGTGGAGGCTCGGGGCCCCGCG
CCAGAGGAAGCACAGAGGGAAAAAGACACACGGATCTCAAAGAAGATGGAGACCATGGGCATCTACTTTGCAA
CACCAGAATGGGTAGCACTCAATGGGCACCGAGGGCCAAGCCCCGGCCAGCTAAAGTACTGGCAGAGCACACG
AGAAATACCGGACCCAAACGAGGACTATCTAGACTACGTGCATGCAGAGAAGAGCCGGTTGGCATCAGAAGAA
CAAATCCTAAGGGCAGCTACGTCGATCTACGGGGCTCCAGGACAGGCAGAGCCACCCCAAGCTTTCATAGACG
AAGTTGCCAAAGTCTATGAAATCAACCATGGACGTGGCCCAAACCAAGAACAGATGAAAGATCTGCTCTTGAC
TGCCATGGAGATGAAGCATCGCAATCCCAGGCGGGCTCTACCAAAGCCCAAGCCAAAACCCAATGCTCCAACA
CAGAGACCCCCTGGTCGGCTGGGCCGCTGGATCAGGACCGTCTCTGATGAGGACCTTGAGTGATCATCCTG
```

Classic IBDV (FD181) VP3 Amino Acid Sequence
SEQ ID NO: 14
```
MAASEFKETPELESAVRAMEAAANVDPLFQSALSVFMWLEENGIVTDMANFALSDPNAHRMRNFLANAPQAGS
KSQRAKYGTAGYGVEARGPAPEEAQREKDTRISKKMETMGIYFATPEWVALNGHRGSPGQLKYWQSTREIPD
PNEDYLDYVHAEKSRLASEEQILRAATSIYGAPGQAEPPQAFIDEVAKVYEINHGRGPNQEQMKDLLLTAMEM
KHRNPRRALPKPKPKPNAPTQRPPGRLGRWIRTVSDEDLE*
``` vvIBDV (Isr4) VP3 Nucleotide Sequence
SEQ ID NO: 15
```
GTACCTGATCACCATGGCTGCATCAGAGTTCAAAGAGACCCCCGAACTCGAGAGTGCCGTCAGAGCAATGGAA
GCAGCAGCCAACGTGGACCCACTATTCCAATCTGCACTCAGTGTGTTCATGTGGCTGGAAGAGAATGGGATTG
```

```
-continued
TGACTGACATGGCCAACTTCGCACTCAGCGACCCGAACGCCCATCGGATGCGAAATTTTCTTGCAAACGCACC
ACAAGCAGGCAGCAAGTCGCAAAGGGCCAAGTACGGGACAGCAGGCTACGGAGTGGAGGCTCGGGGCCCCACA
CCAGAGGAAGCACAGAGGGAAAAAGACACACGGATCTCAAAGAAGATGGAGACCATGGGCATCTACTTTGCAA
CACCAGAATGGGTAGCACTCAATGGGCACCGAGGGCCAAGCCCCGGCCAGCTAAAGTACTGGCAGAACACACG
AGAAATACCGGACCCAAACGAGGACTATCTAGACTACGTGCATGCAGAGAAGAGCCGGTTGGCATCAGAAGAA
CAAATCCTAAGGGCAGCTACGTCGATCTACGGGGCTCCAGGACAGGCAGAGCCACCCCAGGCTTTCATAGACG
AAGTTGCCAAAGTCTATGAAATCAACCATGGACGTGGCCCAAACCAAGAACAGATGAAAGATCTGCTCTTGAC
TGCGATGGAGATGAAGCATCGCAATCCCAGGCGGGCTCTACCAAAGCCCAAGCCGAAACCCAATGCTCCAACA
CAGAGACCCCCTGGTCGGCTGGGCCGCTGGATCAGGACCGCCTCTGATGAGGACCTTGAGTGATCATCCTG vvIBDV (Isr4) VP3 Amino Acid Sequence
                                                               SEQ ID NO: 16
MAASEFKETPELESAVRAMEAAANVDPLFQSALSVFMWLEENGIVTDMANFALSDPNAHRMRNFLANAPQAGS
KSQRAKYGTAGYGVEARGPTPEEAQREKDTRISKKMETMGIYFATPEWVALNGHRGPSPGQLKYWQNTREIPD
PNEDYLDYVHAEKSRLASEEQILRAATSIYGAPGQAEPPQAFIDEVAKVYEINHGRGPNQEQMKDLLLTAMEM
KHRNPRRALPKPKPKPNAPTQRPPGRLGRWIRTASDEDLE*

Classic IBDV (FD181) pVP2 Nucleotide Sequence
                                                               SEQ ID NO: 17
AACGATGATCACGATGACAAACCTGTCAGATCAAACCCAACAGATTGTTCCGTTCATACGGAGCCTTCTGATG
CCAACAACCGGACCGGCGTCCATTCCGGACGACACCCTGGAGAAGCACACTCTCAGGTCAGAGACCTCGACCT
ACAATTTGACTGTGGGGGACACAGGGTCAGGGCTAATTGTCTTTTTCCCTGGATTCCCTGGCTCAATTGTGGG
TGCTCACTACACACTGCAGAGCAATGGGAACTACAAGTTCGATCAGATGCTCCTGACTGCCCAGAACCTACCG
GCCAGTTACAACTACTGCAGGCTAGTGAGTCGGAGTCTCACAGTGAGGTCAAGCACACTTCCTGGTGGCGTTT
ATGCACTAAACGGCACCATAAACGCCGTGACCTTCCAAGGAAGCCTGAGTGAACTGACAGATGTTAGCTACAA
TGGGTTGATGTCTGCAACAGCCAACATCAACGACAAAATTGGGAACGTTCTAGTAGGGGAAGGGGTCACCGTC
CTCAGCTTACCCACATCATATGATCTTGGGTATGTGAGGCTTGGTGACCCCATTCCCGCAATAGGGCTTGACC
CAAAAATGGTAGCCACATGTGACAGCAGTGACAGGCCCAGAGTCTACACCATAACTGCAGCCGATGATTACCA
ATTCTCATCACAGTACCAACCAGGTGGGGTAACAATCACACTGTTCTCAGCCAACATTGATGCCATCACAAGC
CTCAGCGTTGGGGGAGAGCTCGTGTTTCAAACAAGCGTCCACGGCCTTGTACTGGGCGCCACCATCTACCTCA
TAGGCTTTGATGGGACAGCGGTAATCACCAGGGCTGTGGCCGCAAACAATGAGCTGACGACCGGCACCGACAA
CCTTTTGCCATTCAATCTTGTGATTCCAACAAACGAGATAACCCAGCCAATCACATCCATCAAACTGGAGATA
GTGACCTCCAAAAGTGGTGGTCAGGCAGGGGATCAGATGTCATGGTCCGCAAGAGGGAGCCTAGCAGTGACGA
TCCATGGTGGCAACTATCCAGGGGCCCTCCGTCCCGTCACGCTAGGTGCTACGAAAGAGTGGCAACAGGATC
CGTCGTTACGGTCGCTGGGGTGAGCAACTTCGAGCTGATCCCAAATCCTGAACTAGCAAAGAACCTGGTTACA
GAATACGGCCGATTTGACCCAGGAGCCATGAACTACACAAAATTGATACTGAGTGAGAGGGACCGTCTTGGCA
TCAAGACCGTCTGGCCAACAAGGGAGTACACTGACTTTCGTGAATACTTCATGGAGGTGGCCGACCTCAACTC
TCCCCTGAAGATTGCAGGAGCATTCGGCTTCAAAGACATAATCCGGGCCATAAGGAGGATAGCTGTGCCGGTG
GTCTCCACATTGTTCCCACCTGCCGCTCCCCTAGCCCATGCAATTGGGGAAGGTGTAGACTACCTGCTGGGCG
ATGAGGCACAGGCTGCTTCAGGAACTGCTCGAGCCGCGTCAGGAAAAGCAAGAGCTGCCTCGGGCCGCATAAG
GCAGCTGACTCTCGCCGCCGACAAGGGGTGATCAGTAGTA Classic IBDV (FD181) pVP2 Amino Acid Sequence
                                                               SEQ ID NO: 18
MTNLSDQTQQIVPFIRSLLMPTTGPASIPDDTLEKHTLRSETSTYNLTVGDTGSGLIVFFPGFPGSIVGAHYT
LQSNGNYKFDQMLLTAQNLPASYNYCRLVSRSLTVRSSTLPGGVYALNGTINAVTFQGSLSELTDVSYNGLMS
ATANINDKIGNVLVGEGVTVLSLPTSYDLGYVRLGDPIPAIGLDPKMVATCDSSDRPRVYTITAADDYQFSSQ
YQPGGVTITLFSANIDAITSLSVGGELVFQTSVHGLVLGATIYLIGFDGTAVITRAVAANNELTTGTDNLLPF
NLVIPTNEITQPITSIKLEIVTSKSGGQAGDQMSWSARGSLAVTIHGGNYPGALRPVTLVAYERVATGSVVTV
AGVSNFELIPNPELAKNLVTEYGRFDPGAMNYTKLILSERDRLGIKTVWPTREYTDFREYFMEVADLNSPLKI
AGAFGFKDIIRAIRRIAVPVVSTLFPPAAPLAHAIGEGVDYLLGDEAQAASGTARAASGKARAASGRIRQLTL
AADKG*

Variant IBDV (T1) pVP2 Nucleotide Sequence
                                                               SEQ ID NO: 19
AACGATGATCACGATGACAAACCTGTCAGATCAAACCCAACAGATTGTTCCGTTCATACGGAGCCTTCTGATG
CCAACAACCGGACCGGCGTCCATTCCGGACGACACCCTGGAGAAGCACACTCTCAGGTCAGAGACCTCGACCT
ACAATTTGACTGTGGGGACACAGGGTCAGGGCTAATTGTCTTTTTCCCTGGATTCCCTGGCTCAATTGTGGG
TGCTCACTACACACTGCAGAGCAATGGGAACTACAAGTTCGATCAGATGCTCCTGACTGCCCAGAACCTACCG
GCCAGCTACAACTACTGCAGGCTAGTGAGTCGGAGTCTCACAGTAAGGTCAAGCACACTCCCTGGTGGCGTTT
ATGCACTAAACGGCACCATAAACGCCGTGACCTTCCAAGGAAGCCTGAGTGAACTGACAGATGTTAGCTACAA
TGGGTTGATGTCTGCAACAGCCAACATCAACGACAAAATTGGGAACGTTCTAGTAGGGGAAGGGGTAACAGTC
CTCAGCTTACCCACATCATATGATCTTGGGTATGTGAGGCTTGGTGACCCCATACCTGCTATAGGACTTGACC
CAAAAATGGTAGCTACATGTGACAGCAGTGACAGGCCCAGAGTCTACACCATAACTGCAGCTGATAATTACCA
GTTCTCATCACAGTACCAAACAGGTGGGGTAACAATCACACTGTTCTCAGCCAACATTGATGCCATCACAAGT
CTCAGCGTTGGGGGAGAGCTTGTGTTCAAACAAGCGTCCAAAACCTTGTACTGGGTGCCACCATCTACCTTA
TAGGCTTTGATGGGACTGCGGTAATCACCAGAGCTGTGGCCGCAAACAATGGGCTGACGGCCGGCATCGACAA
TCTTATGCCATTCAACCTTGTGATTCCAACCAATGAGATAACCCAGCCAATCACATCCATCAAACTAGAAGATA
GTGACCTCCAAAAGCAATGGGCAGGCAGAGGATCAGATGTCNTGGTCGGCAAGTGGGAGCCTGGCAGTGACGA
TCCATGGTGGCAACTATCCAGGAGCCCTCCGTCCCGTCACACTGGTGGCCTACAAAGAGTGGCAACAGGATC
TGTCGTTACGGTCGCAGGGGTGAGCAACTTCGAGTGATCCCAAATCCTGAACTGGCAAAGAACCTGGTTCACA
GAATACGGCCGATTTGACCCAGGAGCCATGAACTACACAAAATTGATACTGAGTGAGAGGGACCGTCTTGGCA
TCAAGACCGTCTGGCCAACAAGGGAGTACACTGACTTTCGTGAGTACTTCATGGAGGTGGCCGACCTCAACTC
TCCCCTGAAGATTGCAGGAGCATTTGGATTCAAGGACATAATCCGGGCCATAAGGAGGATAGCTGTGCCGGTG
GTCTCTACATTGTTCCCACCTGCCGCTCCTCTAGCCCATGCAATTGGGGAAGGTGTAGACTACCTGCTGGGCG
ATGAGGCACAGGCTGCTTCAGGAACTGCTCGAGCCGCGTCAGGAAAAGCAAGGGCTGCCTCAGGCCGCATAAG
GCAGCTGACTCTCGCCGCCGACAAGGGGTGATCAGTAGT Variant IBDV (T1) pVP2 Amino Acid Sequence
                                                               SEQ ID NO: 20
MTNLSDQTQQIVPFIRSLLMPTTGPASIPDDTLEKHTLRSETSTYNLTVGDTGSGLIVFFPGFPGSIVGAHYT
```

-continued

LQSNGNYKFDQMLLTAQNLPASYNYCRLVSRSLTVRSSTLPGGVYALNGTINAVTFQGSLSELTDVSYNGLMS
ATANINDKIGNVLVGEGVTVLSLPTSYDLGYVRLGDPIPAIGLDPKMVATCDSSDRPRVYTITAADNYQFSSQ
YQTGGVTITLFSANIDAITSLSVGGELVFKTSVQNLVLGATIYLIGFDGTAVITRAVAANNGLTAGIDNLMPF
NLVIPTNEITQPITSIKLEIVTSKSNGQAEDQMSWSASGSLAVTIHGGNYPGALRPVTLVAYERVATGSVVTV
AGVSNFELIPNPELAKNLVTEYGRFDPGAMNYTKLILSERDRLGIKTVWPTREYTDFREYFMEVADLNSPLKI
AGAFGFKDIIRAIRRIAVPVVSTLFPPAAPLAHAIGEGVDYLLGDEAQAASGTARAASGKARAASGRIRQLTL
AADKG* vvIBDV (Pf33) pVP2 Nucleotide Sequence
SEQ ID NO: 21
AACGATGATCACGATGACAAACCTGTCAGATCAAACCCAACAGATTGTTCCGTTCATACGGAGCCTTCTGATG
CCAACAACCGGACCGGCGTCCATTCCGGACGACACCCTAGAGAAGCACACTCTCAGGTCAGAGACCTCGACCT
ACAATTTGACTGTGGGGACACAGGGTCAGGGCTAATTGTCTTTTTCCCTGGTTTCCCTGGCTCAATTGTGGG
TGCTCACTACACACTGCAGAGCAATGGGAGCTACAAGTTCGATCAGATGCTCCTGACTGCCCAGAACCTACCG
GCCAGCTACAACTACTGCAGGCTAGTGAGTCGGAGTCTCACAGTGAGGTCAAGCACACTCCCTGGTGGCGTTT
ATGCTCTAAATGGCACCATAAACGCCGTGACCTTCCAAGGAAGCCTGAGTGAACTGACAGATGTTAGCTACAA
TGGGTTGATGTCTGCAACAGCCAACATCAACGACAAAATCGGGAACGTCCTAGTAGGGGAAGGGGTAACAGTC
CTCAGCTTACCTACATCATACGATCTTGGGTATGTGAGACTCGGTGACCCCATTCCCGCTATAGGGCTCGACC
CAAAAATGGTAGCAACATGTGACAGCAGTGACAGACCCAGAGTCTACACCATAACTGCAGCCGATGATTACCA
ATTCTCATCACAGTACCAAGCAGGTGGGGTAACAATCACACTGTTCTCAGCTAATATCGATGCCATCACAAGC
CTCAGCATCGGGGGGAACTCGTGTTTCAAACAAGCGTCCAAGGCCTCATACTGGGTGCTACCATCTACCTTA
TAGGCTTTGATGGGACTGCGGTAATCACCAGAGCTGTGGCAGCAGACAATGGGCTGACAGCTGGCATCGACAA
CCTTATGCCATTCAACATTGTGATTCCAACCAGCGAGATAACCCAGCCAATCACATCCATCAAACTGGAGATA
GTGACCTCCAAAGTGGTGGTCAGGCGGGGATCAGATGTCATGGTCCGCAAGTGGGAGCCTAGCAGTGACGA
TCCACGGTGGCAACTACCCAGGGGCCCTCCGTCCCGTCACACTAGTAGCCTATGAAAGAGTGGCAACAGGGTC
TGTCGTTACGGTCGCTGGGGTGAGCAACTTCGAGCTGATCCCAAATCCTGAACTAGCAAAGAACCTGGTCACA
GAATACGGCCGATTTGACCCAGGGGCTATGAACTACACAAAATTAATACTGAGTGAGAGGGACCGTCTTGGCA
TCAAGACCGTATGGCCAACGAGGGAGTACACTGACTTTCGCGAGTACTTCATGGAGGTGGCCGACCTCAACTC
TCCCCTGAAGATTGCAGGAGCATTTGGCTTCAAAGACATAATTCGGGCTCTAAGGAGGATAGCTGTGCCGGTG
GTCTCTACACTGTTCCCACCAGCCGCTCCCCTAGCCCATGCAATTGGGGAAGGTGTAGACTACCTGCTGGGCG
ATGAGGCACAGGCTGCTTCAGGAACTGCTCGAGCCGCGTCAGGAAAAGCAAGAGCTGCCTCAGGTCGCATAAG
GCAGCTAACTCTCGCCGCCGACAAGGGGTGATCAGTAGTA vvIBDV (Pf33) pVP2 Amino Acid Sequence
SEQ ID NO: 22
MTNLSDQTQQIVPFIRSLLMPTTGPASIPDDTLEKHTLRSETSTYNLTVGDTGSGLIVFFPGFPGSIVGAHYT
LQSNGSYKFDQMLLTAQNLPASYNYCRLVSRSLTVRSSTLPGGVYALNGTINAVTFQGSLSELTDVSYNGLMS
ATANINDKIGNVLVGEGVTVLSLPTSYDLGYVRLGDPIPAIGLDPKMVATCDSSDRPRVYTITAADDYQFSSQ
YQAGGVTITLFSANIDAITSLSIGGELVFQTSVQGLILGATIYLIGFDGTAVITRAVAADNGLTAGTDNLMPF
NIVIPTSEITQPITSIKLEIVTSKSGGQAGDQMSWSASGSLAVTIHGGNYPGALRPVTLVAYERVATGSVVTV
AGVSNFELIPNPELAKNLVTEYGRFDPGAMNYTKLILSERDRLGIKTVWPTREYTDFREYFMEVADLNSPLKI
AGAFGFKDIIRALRRIAVPVVSTLFPPAAPLAHAIGEGVDYLLGDEAQAASGTARAASGKARAASGRIRQLTL
AADKG*

Serotype 2 IBDV (OH) pVP2 Nucleotide Sequence
SEQ ID NO: 23
GGGAATTCACTAGTGATTTTCGATGATCACGATGACAAACCTGTCAGATCACACCCAACAGATTGTTCCGTTC
ATACGGAGCCTTCTGATGCCAACGACCGGACCGGCGTCCATCCCGGACGACACCCTGGAGAAGCACACACTCA
GGTCCGAAACCTCGACCTACAACTTGACTGTCGGGGACACAGGGTCAGGACTAATTGTCTTTTTCCCTGGATT
CCCTGGTTCAGTTGTAGGTGCTCACTACACACTGCAGAGCAGTGGGAGCTACAGTTCGACCAGATGCTCCTG
ACAGCGCAGAACCTGCCTGCGAGCTACAACTATTGCAGACTAGTGAGCAGGAGCCTAACCGTGCGGTCAAGCA
CACTCCCTGGTGGCGTTTATGCTCTAAATGGGACCATAAACGCGTGACCTTCCAAGGAAGCCTGAGTGAGTT
GACTGACTACAGCTACAACGGGCTGATGTCAGCCACTGCAAACATCAACGACAAGATCGGGAATGTCCTTGTT
GGGGAAGGGGTGACTGTCCTAAGTCTACCAACCTCATATGACCTCAGTTATGTGAGGCTTGGCGACCCCATCC
CAGCAGCAGGACTTGACCCAAAGTTGATGGCCACGTGCGACAGTAGTGATAGACCCAGAGTCTACACAGTAAC
AGCCGCTGATGAGTACCAATTCTCGTCGCAACTCATCCCAAGTGGAGTGAAGACTACACTGTTCACCGCCAAC
ATCGATGCTCTTACAAGCCTCAGTGTTGGTGGTGAGCTTATCTTCAGCCAAGTAACGATCCAAAGCATTGAAG
TGGACGTCACCATTTACTTCATTGGGTTCGACGGGACAGAGGTCACAGTCAAAGCTGTTGCAACAGACTTTGG
GCTGACAACTGGGACGAACAACCTTGTGCCATTCAACCTGGTGGTCCCAACAAGTGAGATCACCCAACCCATC
ACTTCCATGAAACTAGAGGTAGTCACCCATAAAGAGGAGGCACTGCTGGCGATCCGATATCATGGACAGTGA
GCGGGACACTAGCTGTGACAGTGCACGGAGGCAACTATCCTGGGGCTCTCCGTCCCGTCACCCTAGTGGCCTA
TGAGCGAGTGGCAGCAGGATCCGTCGTCACAGTTGCAGGGGTGAGCAACTTCGAGCTGATCCCAAACCCTGAG
CTTGCCAAGAACCTAGTCACAGAATATGGCCGATTTGACCCCGGAGCGATGAACTACACACCAAACTAATACTGA
GTGAGAGAGATCGTCTAGGCATAAAGACTGTCTGGCCAACCAGGGAGTACACTGACTTTAGAGAGTACTTCAT
GGAAGTTGCCGATCTCAACTCACCCTTAAAGATTGCAGGTGCGTTTGGTTTTAAGGACATAATCCGAGCCATC
CGGAAGATTGCGGTACCAGTGGTATCCACACTCTTCCCACCAGCTGCACCCCTAGCCCATGCAATCGGAGAAG
GTGTGGATTACCTTCTGGGCGATGAGGCCCAGGCAGCCTCAGGGACGGCTCGAGCCGCGTCAGGAAAAGCCAG
GGCTGCCTCAGGAAGAATAAGGCAGCTGACTCTCGCCGCCGACAAGGGGT Serotype 2 IBDV (OH) pVP2 Amino Acid Sequence
SEQ ID NO: 24
MTNLSDHTQQIVPFIRSLLMPTTGPASIPDDTLEKHTLRSETSTYNLTVGDTGSGLIVFFPGFPGSVVGAHYT
LQSSGSYQFDQMLLTAQNLPASYNYCRLVSRSLTVRSSTLPGGVYALNGTINAVTFQGSLSELTDYSYNGLMS
ATANINDKIGNVLVGEGVTVLSLPTSYDLSYVRLGDPIPAAGLDPKLMATCDSSDRPRVYTVTAADEYQFSSQ
LIPSGVKTTLFTANIDALTSLSVGGELIFSQVTIQSIEVDVTIYFIGFDGTEVTVKAVATDFGLTTGTNNLVP
FNLVVPTSEITQPITSMKLEVVTHKRGGTAGDPISWTVSGTLAVTVHGGNYPGALRPVTLVAYERVAAGSVVT
VAGVSNFELIPNPELAKNLVTEYGRFDPGAMNYTKLILSERDRLGIKTVWPTREYTDFREYFMEVADLNSPLK
IAGAFGFKDIIRAIRKIAVPVVSTLFPPAAPLAHAIGEGVDYLLGDEAQAASGTARAASGKARAASGRIRQLT
LAADKG*

What is claimed is:

1. A polyvalent VP2 trimer of infectious bursa disease virus (IBDV), wherein the polyvalent VP2 trimer comprises three VP2 monomers, and wherein at least one of the VP2 monomers is from a classic strain of IBDV, and wherein at least one of the VP2 monomers is from a variant strain of IBDV.

2. The polyvalent VP2 of claim 1, wherein the VP2 monomers are each independently from an IBDV strain selected from the group consisting of USA08MD34p, Mo195, UPM97/61, UPM94/273, OKYM, UK661, IBDKS, D6948, BD3/99, TASIK, Chinju, HK46, SH95, Gx, SDH1, T09, D78, Cu-IM, P2, CT, CEF94, PBG 98, JD1, HZ2, TAD Gumboro, Delvax Gumboro LZD, IBD-VAC, 89163, Edgar, UK661, rA, rB, VarE, Del-A, VarGLS, V1, GER, USA06CA440, D78, Bursine, F52/70, Cu-1, V877, Burs706, CA-D495, CA-K785, IBDV strain 02015.1, and GX.

3. The polyvalent VP2 of claim 1, wherein at least one of the VP2 monomers is from variant strain USA08MD34p and at least one of the VP2 monomers is from IBDV classic strain Mo195.

4. A virus like particle (VLP) comprising VP3 proteins from at least one strain of infectious bursa disease virus (IBDV) and the polyvalent VP2 trimer of claim 1.

5. The VLP of claim 4, wherein at least one of the VP2 monomers is from an IBDV selected from the group consisting of USA08MD34p, Mo195, UPM97/61, UPM94/273, OKYM, UK661, IBDKS, D6948, BD3/99, TASIK, Chinju, HK46, SH95, Gx, SDH1, T09, D78, Cu-IM, P2, CT, CEF94, PBG-98, JD1, HZ2, TAD Gumboro, Delvax Gumboro LZD, IBD-VAC, 89163, Edgar, UK661, rA, rB, VarE, Del-A, VarGLS, V1, GER, USA06CA440, D78, Bursine, F52/70, Cu-1, V877, Burs706, CA-D495, CA-K785, IBDV strain 02015.1, and GX.

6. The VLP of claim 5, wherein at least one of the VP2 monomers is from IBDV variant strain USA08MD34p.

7. The VLP of claim 6, wherein at least one of the VP2 monomers is from IBDV classic strain Mo195.

8. The VLP of claim 5, wherein at least one of the VP2 monomers is from an IBDV strain which is not IBDV variant strain USA08MD34p and is not IBDV classic strain Mo195.

9. The VLP of claim 5, wherein at least one of the VP2 monomers is from IBDV classic strain Mo195 and wherein at least one of the VP2 monomers is from IBDV variant strain USA08MD34p.

10. The VLP of claim 5, comprising two VP2 monomers of IBDV variant strain USA08MD34p and one VP2 monomer of IBDV classic strain Mo195.

11. The VLP of claim 5, comprising one VP2 monomer of IBDV variant strain USA08MD34p and two VP2 monomers of IBDV classic strain Mo195.

12. The VLP of claim 4, wherein the VP3 proteins are from IBDV variant strain USA08MD34p.

13. The VLP of claim 4, wherein the VP3 proteins are from more than one IBDV strain.

14. A composition comprising the VLP of claim 4, and a pharmaceutically acceptable carrier.

15. An isolated host cell expressing the VLP of claim 4.

16. The cell of claim 15, wherein the cell is an insect cell.

17. The cell of claim 16, wherein the insect cell is a Sf9 cell.

18. A method of eliciting an immune response against IBDV in a subject comprising administering to the subject a composition comprising the VLP of claim 4.

19. The method of claim 18, wherein the subject is an avian.

20. The method of claim 19, wherein the avian is a chicken.

21. The method of claim 18, further comprising administering to the subject a virulent IBDV to monitor the immune response.

22. The method of claim 18, wherein the virulent IBDV is selected from the group consisting of the V1 variant virus and the STC strain.

23. The method of claim 18, wherein the composition is administered at a dose of between 25-50 ug.

24. The method of claim 18, wherein the composition is administered in a single dose.

25. The method of claim 18, wherein the composition is administered in two doses.

26. The method of claim 25, wherein the two doses are administered between a 10-21 day interval.

27. The method of any of claim 18, wherein the composition is administered in a mist.

\* \* \* \* \*